(12) United States Patent
Kato et al.

(10) Patent No.: US 8,990,024 B2
(45) Date of Patent: Mar. 24, 2015

(54) FLUORESCENCE INTENSITY COMPENSATION METHOD AND FLUORESCENCE INTENSITY CALCULATION DEVICE

(75) Inventors: Yasunobu Kato, Kanagawa (JP); Yoshitsugu Sakai, Kanagawa (JP)

(73) Assignee: Sony Corporation, Tokyo (JP)

( * ) Notice: Subject to any disclaimer, the term of this patent is extended or adjusted under 35 U.S.C. 154(b) by 812 days.

(21) Appl. No.: 13/178,172

(22) Filed: Jul. 7, 2011

(65) Prior Publication Data

US 2012/0010822 A1 Jan. 12, 2012

(30) Foreign Application Priority Data

Jul. 9, 2010 (JP) ................................. 2010-156382

(51) Int. Cl.
*G06F 19/16* (2011.01)
*G06F 19/10* (2011.01)
*G01N 15/14* (2006.01)
(Continued)

(52) U.S. Cl.
CPC ............ *G01N 15/1429* (2013.01); *G01N 21/53* (2013.01); *G01N 21/6428* (2013.01); *G01N 21/645* (2013.01); *G01N 15/1459* (2013.01); *G01N 2021/4707* (2013.01); *G01N 2021/4726* (2013.01); *G01N 2021/6421* (2013.01);
(Continued)

(58) Field of Classification Search
CPC .......... G01N 15/1429; G01N 15/1459; G01N 21/53; G01N 21/6428; G01N 21/645; G01N 2201/1293; G01N 2021/4707; G01N 2021/4726; G01N 2021/6421; G01N 2021/6439
USPC .............................................. 702/19; 378/44
See application file for complete search history.

(56) References Cited

U.S. PATENT DOCUMENTS 6,584,413 B1 * 6/2003 Keenan et al. .................. 702/28
6,675,106 B1 * 1/2004 Keenan et al. .................. 702/28
(Continued)

FOREIGN PATENT DOCUMENTS

| JP | 2003-083894 | 3/2003 |
|----|-------------|--------|
| JP | 2004-286515 | 10/2004 |

(Continued)

OTHER PUBLICATIONS

Straume et al., "Least-Squares Analysis of Fluorescence Data" Topics in Fluorescence Speciroscopy, vol. 2: Principles, edited by Joseph R. Lakowicz. Plenum Press, New York, 1991.*

(Continued)

*Primary Examiner* — Mohamed Charioui
*Assistant Examiner* — John Kuan
(74) *Attorney, Agent, or Firm* — K&L Gates LLP

(57) ABSTRACT

A fluorescence intensity compensation method, includes: receiving, with photodetectors having different input wavelength bands, fluorescence emitted from fluorochromes excited by irradiating light on microparticles multiply-labeled by a plurality of fluorochromes with overlapping fluorescence wavelengths; collecting detected values for the photodetectors; and obtaining a measurement spectrum, by approximating, from the linear sum of single-stain spectrums obtained from microparticles individually labeled with the fluorochromes; wherein approximation of the measurement spectrum by the linear sum of the single-stain spectrums is performed using the restricted least-square method.

6 Claims, 13 Drawing Sheets

(51) Int. Cl.
*G01N 21/53* (2006.01)
*G01N 21/64* (2006.01)
*G01N 21/47* (2006.01)

(52) U.S. Cl.
CPC ...... *G01N2021/6439* (2013.01); *G01N 2201/1293* (2013.01)
USPC .............................................. 702/19; 378/44

(56) References Cited

U.S. PATENT DOCUMENTS

| | | | | |
|---|---|---|---|---|
| 7,400,772 | B1* | 7/2008 | Keenan | 382/232 |
| 7,725,517 | B1* | 5/2010 | Keenan | 708/446 |
| 2008/0212866 | A1* | 9/2008 | Lett et al. | 382/133 |

FOREIGN PATENT DOCUMENTS

| | | |
|---|---|---|
| JP | 2005-036289 | 2/2005 |
| JP | 2005-512051 | 4/2005 |
| JP | 2009-109197 | 5/2009 |
| JP | 2009-233253 | 10/2009 |
| JP | 2009-540322 | 11/2009 |

OTHER PUBLICATIONS

Bro et al., "A Fast Non-Negativity-Constrained Least Squares Algorithm" Journal of Chemometrics, vol. 11, 393-401 (1997).*

Jerilyn A. Timlin, et al., "Imaging Multiple Endogenous and Exogenous Fluorescent Species in Cells and Tissues," Imaging, Manipulation, and Analysis of Biomolecules, Cells, and Tissues IV, edited by Daniel L. Farkas, Dan V. Nicolau, Robert C. Leif, Proc. of SPIE vol. 6088, 608805, (2006). (12 pages).

Japanese Patent Office, Office Action issued in connection with Japanese Patent Application No. 2010-156382, dated Jan. 7, 2014. (3 pages).

Keenan et al., "Algorithms for Constrained Linear Unmixing with Application to the Hyperspectral Analysis of Fluorophore Mixtures," Imaging Spectrometry VIII. Edited by Shen, Sylvia S. Proceedings of the SPIE, vol. 4816, pp. 193-202 (2002). (10 page).

Timlin et al. "Imaging Multiple Endogenous and Exogenous Fluorescent Species in Cells and Tissues," Imaging, Manipulation, and Analysis of Biomolecules, Cells, and Tissues IV, edited by Daniel L. Farkas, Dan V. Nicolau. Robert C. Leif. Proc of SPIE vol. 6088. 608805 (2006). (10 pages).

Haaland et al.. "Multivariate Curve Resolution for Hyperspectral Image Analysis: Applications to Microarray Technology," Spectral Imaging: Instrumentation, Applications, and Analysis II. A. M Levenson, G H. Bearman, A Mahadevan-Jansen, Editors. Proceedings of SPIE vol. 4959, pp. 55-66 (2003). (12 pages).

Benthem et al., "Fast algorithm for the solution of large-scale non-negativity-constrained least squares problems," Journal of Chemometrics, vol. 18, pp. 441-450 (2004). (10 pages).

Benthem et al., "Application of equality constraints on variables during alternating least squares procedures," Journal of Chemometrics, vol. 16, pp. 613-622 (2002). (10 pages).

Bro et al., "Least Squares Algorithms Under Unimodality and Non-Negativity Constraints," Journal of Chemometrics, vol. 12, pp. 223-247 (1998). (26 pages).

European Patent Office, Extended European Search Report, issued in connection with European Patent Application No. 11169278.6, dated Dec. 22, 2011. (7 pages).

Chinese Office Action issued Jun. 30, 2014, for corresponding Chinese Appln. No. 201110185326.2

Communication pursuant to Article 94(3) EPC issued in connection with European Patent Application No. 11169278.6, dated Sep. 18, 2014. (6 pages).

* cited by examiner

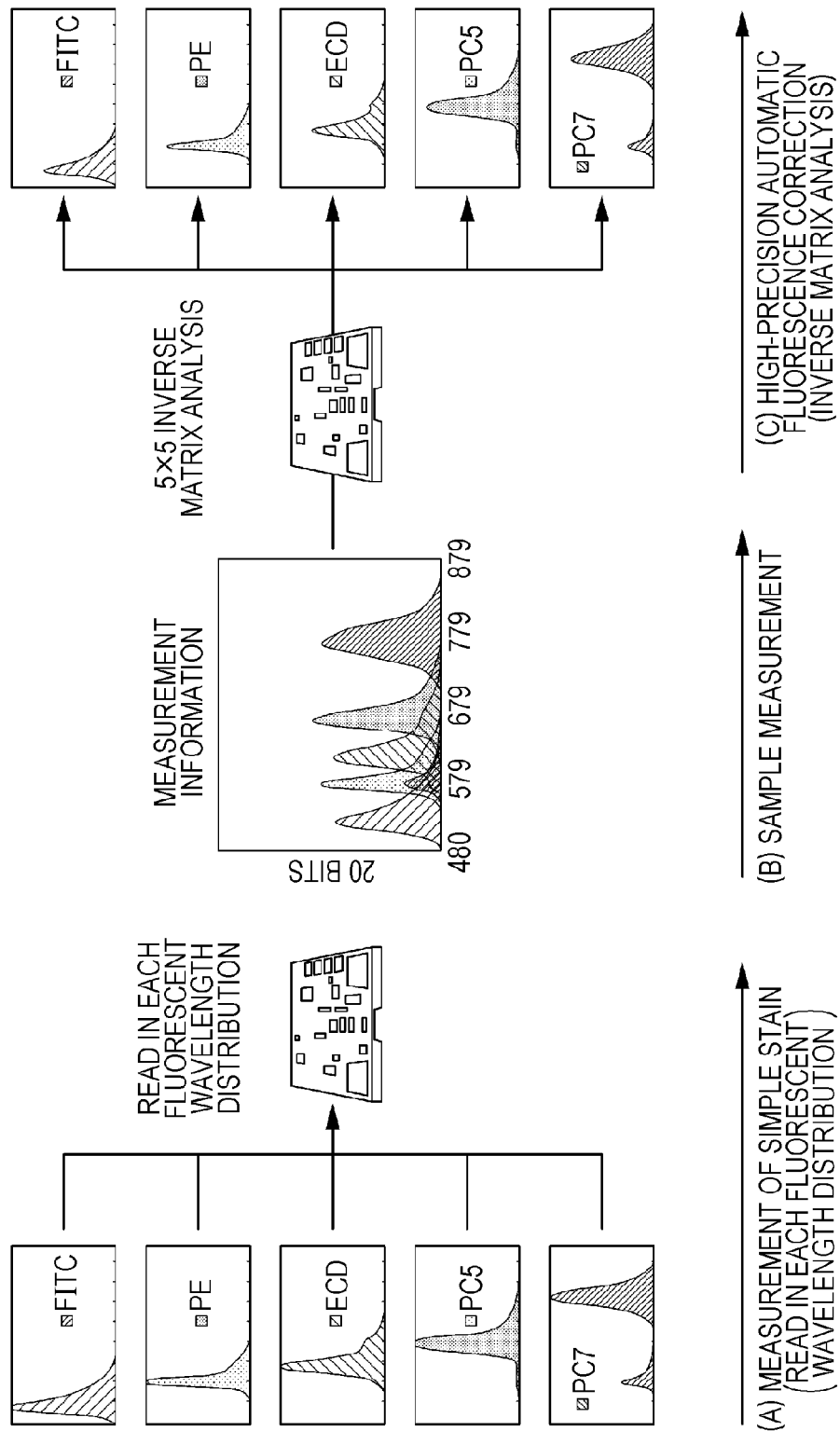

FIG. 13

$$\begin{pmatrix} FL1 \\ FL2 \\ FL3 \\ FL4 \\ FL5 \end{pmatrix} = \begin{pmatrix} a_{11} & a_{21} & a_{31} & a_{41} & a_{51} \\ a_{12} & a_{22} & a_{32} & a_{42} & a_{52} \\ a_{13} & a_{23} & a_{33} & a_{43} & a_{53} \\ a_{14} & a_{24} & a_{34} & a_{44} & a_{54} \\ a_{15} & a_{25} & a_{35} & a_{45} & a_{55} \end{pmatrix}^{-1} \begin{pmatrix} PMT1 \\ PMT2 \\ PMT3 \\ PMT4 \\ PMT5 \end{pmatrix}$$

FL1 TO FL5: TRUE FLUORESCENT INTENSITY OF EACH FLUOROCHROME
$a_n1$ TO $a_n5$: WAVELENGTH DISTRIBUTION RATIO OF FLUOROCHROME n
PMT1 TO PMT5: EACH MEASURED FLUORESCENT INTENSITY

FLUORESCENCE INTENSITY COMPENSATION METHOD AND FLUORESCENCE INTENSITY CALCULATION DEVICE

CROSS REFERENCES TO RELATED APPLICATIONS

The present application claims priority to Japanese Priority Patent Application JP 2010-156382 filed in the Japan Patent Office on Jul. 9, 2010, the entire contents of which are hereby incorporated by reference.

BACKGROUND

The present application relates to a fluorescence intensity compensation method and a fluorescence intensity calculation device. More particularly, the present application relates to a fluorescence intensity compensation method and the like, to accurately calculate the intensity of fluorescence emitted from each of multiple fluorochromes multiply-labeling microparticles.

There are devices according to the related art which measure properties of microparticles (e.g., flow cytometers) which measure the properties of microparticles, by marking microparticles such as cells or the like using fluorochromes, exciting these by laser beam irradiation, and measuring fluorescence intensities and patterns emitted from these fluorochromes. In recent years, multicolor measurement has come to be performed to analyze the properties cells and the like in greater detail, in which microparticles are marked using multiple fluorochromes, and light emitted from each fluorochromes is measured with multiple photodetectors having different input wavelength bands (PD, PMT, etc.). With multicolor measurement, detection of fluorescence is performed by selecting optical filters at the photodetector side in accordance with the fluorescence wavelength of the fluorochromes used.

On the other hand, currently-used fluorochromes (e.g., FITC, PE (phycoerythrin), APC (allophycocyanin), etc.) have mutually-overlapping wavelength bands in the fluorescence spectrum. Accordingly, in the event of combining these fluorochromes to perform multicolor measurement, fluorescence from unintended fluorochromes may leak into the photodetectors even if the fluorescence emitted from the fluorochromes is separated into wavelength bands by optical filters. If leakage of fluorescence occurs, there will be discrepancy between the fluorescence intensity measured at the detectors and the true fluorescence intensity from the intended fluorochromes, leading to measurement error.

Fluorescence compensation is performed in which fluorescence intensity equivalent to the leakage is subtracted from the fluorescence intensity measured at the photodetector is performed in order to compensate for the measurement error. Fluorescence compensation involves applying electrical or mathematical correction to pulses so that the fluorescence intensity measured at the photodetector is the true fluorescence intensity from the intended fluorochrome.

A technique is being used as a method for mathematically performing fluorescence compensation in which the true fluorescence intensity from the intended fluorochromes is calculated, by representing the fluorescence intensities (detected values) measured at the photodetectors are represented as vectors, and an inverse matrix of a preset leakage matrix is applied to these vectors (see FIGS. 12 and 13, and Japanese Unexamined Patent Application Publication No. 2003-83894). This leakage matrix is created by analyzing fluorescence wavelength distribution of microparticles single-labeled individually with the fluorochromes, with the fluorescence wavelengths of the fluorochromes arrayed as column vectors. An inverse matrix of a leakage matrix is also called a "compensation matrix". FIGS. 12 and 13 show an example of performing five-color measurement using five types of fluorochromes (FITC, PE, ECD, PC5, PC7) and five photodetectors.

SUMMARY

With the fluorescence compensation method using a compensation matrix, there are cases where the fluorescence intensity following compensation is negative. This is due to noise included in the detection values of each photodetector affecting the matrix computation. However, in reality, it is inconceivable that the fluorescence intensity from the fluorochromes would be a negative value. Further, the fluorescence intensity from a certain fluorochromes being calculated as a negative value means at the same time that there is error in the positive direction in the calculation values of the fluorescence intensities of other fluorochromes.

In the event that there is a subpopulation within a microparticle population to be analyzed, regarding which the fluorescence intensity for a certain fluorochromes exhibits a negative value, the subpopulation is not plotted on a two-dimensional correlation diagram (cytogram) where the fluorescence intensity of this fluorochrome is plotted along a logarithmic axis (log scale). Accordingly, the user may receive an incorrect impression that the number of populations plotted on the two-dimensional correlation diagram has become smaller than actual.

It has been found desirable to provide a technique to accurately calculate fluorescence intensities from the fluorochromes and present these to the user, in a case of performing multicolor measurement of microparticles marked with multiple fluorochromes using multiple photodetectors.

According to an embodiment, a fluorescence intensity compensation method includes: receiving, with photodetectors having different input wavelength bands, fluorescence emitted from fluorochromes excited by irradiating light on microparticles multiply-labeled by a plurality of fluorochromes with overlapping fluorescence wavelengths; collecting detected values for the photodetectors; and obtaining a measurement spectrum, by approximating, from the linear sum of single-stain spectrums obtained from microparticles individually labeled with the fluorochromes; wherein approximation of the measurement spectrum by the linear sum of the single-stain spectrums is performed using the restricted least-square method.

The intensity of fluorescence emitted from each fluorochrome may be calculated by obtaining a parameter $x_j$ (j=1 through M) where an evaluation function shown in the following Expression (1) satisfies the following Expression (2) and also is the smallest value. By performing compensation computation with the constraint of Expression (2) provided, the problems of measurement error due to fluorescence intensities from fluorochromes being calculated as negative values, and reduction in populations on two-dimensional correlation diagrams (cytograms), can be solved.

$$\chi^2 = \sum_{i=1}^{N} \left( \frac{p_i - \sum_{j=1}^{M} s_{ij} \cdot x_j}{\sigma_i} \right)^2 \quad (1)$$

$$x_j \geq U_j \quad (2)$$

where $S_{ij}$ represents the detected value of the i'th photodetector in the single-stain spectrum of the j'th fluorochrome, $p_i$ represents the detected value of the i'th photodetector in the measurement spectrum, $\sigma_i$ represents the inverse number of the weight as to the detected value of the i'th photodetector, and $U_j$ represents the lower limit value of the fluorescence intensity of each fluorochrome to be calculated.

The parameter $x_j$ (j=1 through M) may be obtained by solving the quadratic programming problem in the following Expressions (3) through (5)

$$\text{Minimize } \|Sx - p\|_2 \quad (3)$$

$$\text{subject to } Ax \leq b \quad (4)$$

$$x \geq 0 \quad (5)$$

$$A = \begin{pmatrix} -1 & 0 & \cdots & 0 \\ 0 & -1 & & 0 \\ \vdots & & \ddots & \vdots \\ 0 & 0 & \cdots & -1 \end{pmatrix} \quad (6)$$

$$b = \begin{pmatrix} -U_1 \\ -U_2 \\ \vdots \\ -U_M \end{pmatrix} \quad (7)$$

where S represents an N×M order matrix with $s_{ij}$ as elements, x represents an M order matrix with $x_j$ as elements, p represents an N'th order vector with $p_i$ as elements, A is set as an M×M order matrix and b as an M×1 order matrix, and $U_1$ through $U_M$ represent the lower limit value.

In the above Expression (2), either an undyed average value $V_j$ of the j'th fluorochrome obtained from the average value of detection values from each of the photodetectors, obtained by irradiating light on microparticles not marked with the j'th fluorochrome, a random number generated following an undyed probability density function $F_j(U_j)$ of the j'th fluorochrome obtained from a probability density function of detection values, may be used as the lower limit $U_j$, or, the undyed average value $V_j$ and undyed standard deviation $\rho_j$ of the of the j'th fluorochrome may be obtained from the average value and dispersion of detection values from each of the photodetectors, obtained by irradiating light on microparticles not marked with the j'th fluorochrome, with a random number, generated following the undyed probability density function $F_j(U_j)$ in Expression (9) being used as the lower limit $U_j$.

Also, the parameter $x_j$ (j=1 through M) may be obtained by solving the $$F_j(U_j) = \frac{1}{\sqrt{2\pi}\,\rho_j} e^{-\frac{(U_j - V_j)^2}{2\rho_j^2}} \quad (9)$$

quadratic programming problem in the following Expressions (10) and (11) without the linear constraint of Expression (4) above.

$$\text{Minimize } \|Sx - p\|_2 \quad (10)$$

$$\text{subject to } x \geq 0 \quad (11)$$

where S represents an N×M order matrix with $s_{ij}$ as elements, x represents an M order matrix with $x_j$ as elements, and p represents an N'th order vector with $p_i$ as elements.

Further, in the case of solving a quadratic programming problem without the linear constraint of Expression (4) above, the parameter $x_j$ (j=1 through M) may be obtained by solving the quadratic programming problem in the following Expressions (12) and (13), and executing the following Expression (14)

$$\text{Minimize } \|Sx' - (p-u)\|_2 \quad (12)$$

$$\text{subject to } x' \geq 0 \quad (13)$$

$$x = x' + U \quad (14)$$

where S represents an N×M order matrix with $s_{ij}$ as elements, x represents an M order matrix with $x_j$ as elements, p represents an N'th order vector with $p_i$ as elements, u represents an N'th order vector with the average value $v_i$ of detected values from the i'th photodetector, obtained by irradiating light on microparticles unmarked with the j'th fluorochrome, as elements, and U represents an M'th order vector with the undyed average value $V_j$ of the j'th fluorochrome obtained from the average value $v_i$ as elements.

Alternatively, the parameter $x_j$ (j=1 through M) may be obtained by solving the quadratic programming problem in the following Expressions (15) and (16), and executing the following Expression (17)

$$\text{Minimize } \|Sx' - (p-u)\|_2 \quad (15)$$

$$\text{subject to } x' \geq 0 \quad (16)$$

$$x = x' + U \quad (17)$$

where S represents an N×M order matrix with $s_{ij}$ as elements, x represents an M order matrix with $x_j$ as elements, p represents an N'th order vector with $p_i$ as elements, u represents an N'th order vector with the random numbers $u_i$ generated following the probability density function $f_i(u_i)$ of the detection value of the i'th photodetector, obtained by irradiating light on microparticles unmarked with the j'th fluorochrome, as elements, and U represents an M'th order vector with the random numbers $U_j$ generated following the undyed probability density function $F_j(U_j)$ of the j'th fluorochrome obtained from the probability density function $f_i(u_i)$ as elements.)

Further, the parameter $x_j$ (j=1 through M) may be obtained by solving the quadratic programming problem in the following Expressions (20) and (21), and executing the following Expression (22)

$$f_i(u_i) = \frac{1}{\sqrt{2\pi}\,\sigma_i} e^{-\frac{(u_i - v_i)^2}{2\sigma_i^2}} \quad (18)$$

$$F_j(U_j) = \frac{1}{\sqrt{2\pi}\,\rho_j} e^{-\frac{(U_j - V_j)^2}{2\rho_j^2}} \quad (19)$$

$$\text{Minimize } \|Sx' - (p-u)\|_2 \quad (20)$$

$$\text{subject to } x' \geq 0 \quad (21)$$

$$x = x' + U \quad (22)$$

where S represents an N×M order matrix with $s_{ij}$ as elements, x represents an M order matrix with $x_j$ as elements, p represents an N'th order vector with $p_i$ as elements, u represents an N'th order vector with a random number $u_j$ generated by obtaining the average value $V_j$ and dispersion $\sigma_i$ of the of the i'th photodetector obtained by irradiating light on microparticles not marked with the j'th fluorochrome, and generating the random number $u_i$ following the probability density function $f_j(u_j)$ in Expression (18), as the elements, and U represents an M'th order vector having as the elements a random number $U_j$ generated by obtaining the undyed average value $V_j$ and undyed standard deviation $\rho_i$ of the j'th fluorochrome from the average value $v_i$ and dispersion $\sigma_i$ and generating the random number $U_j$ following the probability density function $F_j(U_j)$ in Expression (19).)

According to another embodiment, a fluorescence intensity calculation device includes: a measurement unit configured to receive, with a plurality of photodetectors having different input wavelength bands, fluorescence emitted from fluorochromes excited by irradiating light on microparticles multiply-labeled by a plurality of fluorochromes with overlapping fluorescence wavelengths, collect detected values for the photodetectors, and obtain measurement spectrums; and a calculating unit configured to approximate the measurement spectrum from the linear sum of single-stain spectrums obtained from microparticles individually labeled with the fluorochromes; with the calculating unit performing approximation of the measurement spectrum from the linear sum of the single-stain spectrums using the restricted least-square method.

In the present Specification, the term "microparticle" broadly includes living object related microparticles such as cells, microorganisms, liposomes, and so forth, and synthetic particles such as latex particles, gel particles, industrial particles, and so forth.

Living object related microparticles include chromosomes, liposomes, mitochondria, organelle (cell organelle) and so forth, making up various types of cells. Cells include animal cells (hematocyte type cells) and plant cells. Microorganisms include bacillus such as bacillus coli, viruses such as the tobacco mosaic virus, fungi such as yeast, and so forth. Further, we will say that living object related microparticles include living object related polymers such as nucleic acids, proteins, and compounds thereof. Also, industrial particles may be, for example, organic or non-organic polymeric materials, or metal or the like. Organic polymeric materials include polystyrene, styrene-divinylbenzene, polymethylmethacrylate, and so forth. Non-organic polymeric materials include glass, silica, magnetic materials, and so forth. Metals include gold colloid, aluminum, and so forth. Generally, the shape of these microparticles is normally spherical, but these may be aspherical, and the size and weight thereof are not restricted in particular, either.

Additional features and advantages are described herein, and will be apparent from the following Detailed Description and the figures.

BRIEF DESCRIPTION OF THE FIGURES

FIG. 12 is a diagram for describing a fluorescence compensation method according to the related art using a compensation matrix; and FIG. 13 is a diagram for describing matrix elements of a compensation matrix according to the related art.

DETAILED DESCRIPTION

Figure 1:
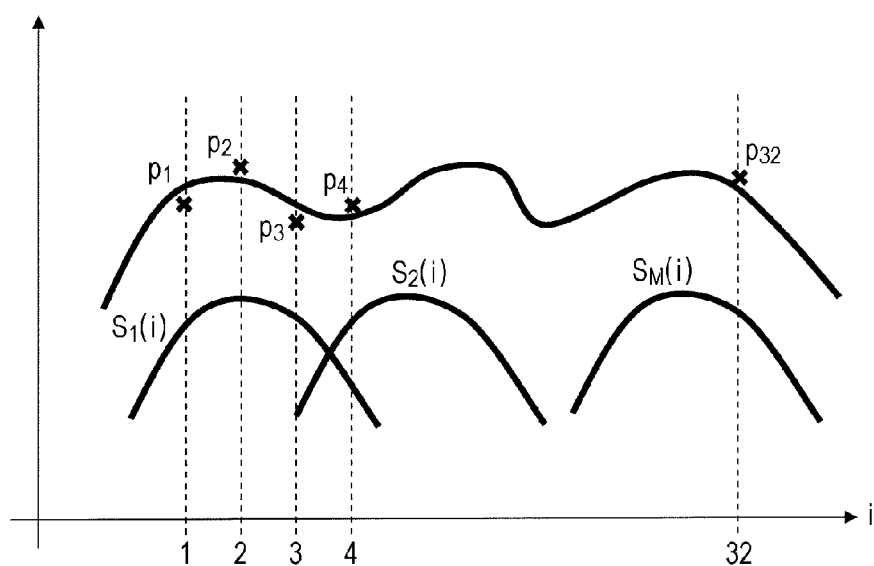
FIG. 1 is a graph for describing an approximation curve obtained by approximation of a measurement spectrum by linear sum of single-stain spectrums.

Embodiments of the present application will be described below in detail with reference to the drawings.

1. Fluorescence Intensity Compensation Method
(1) Measuring Procedures
(2) Calculating Procedures
(2-1) Approximation Curve
(2-2) Restricted Least-Square Method
(2-3) Constrictions (Lower Limit Conditions)
(2-3-1) Average Value as Lower Limit Condition (First Embodiment and Modification Thereof)
(2-3-2) Random Number Following Probability Density Function as Lower Limit Condition (Second Embodiment and Modification Thereof)
(2-3-3) Random Number Following Normal Distribution as Lower Limit Condition (Third Embodiment and Modification Thereof)
(2-3-4) 0 as Lower Limit Condition (Fourth Embodiment)
2. Fluorescence Intensity Calculating Device
1. Fluorescence Intensity Compensation Method The fluorescence intensity compensation method according to an embodiment includes the following two procedures.

Measurement procedure: a procedure to receive, with multiple photodetectors having different input wavelength bands, fluorescence emitted from fluorochromes excited by irradiating light on microparticles multiply-labeled by multiple fluorochromes with overlapping fluorescence wavelengths, collecting detected values for the photodetectors, and obtaining measurement spectrums.

Calculating Procedures: a procedure to approximate, from the linear sum of single-stain spectrums obtained from microparticles individually labeled with the fluorochromes, a measurement spectrum, using the restricted least-square method.

(1) Measuring Procedures

First, microparticles to be measured are multiply-labeled using multiple fluorochromes. Fluorochrome labeling of microparticles can be performed using techniques according to the related art. For example, in the event that the objects of measurement are cells, fluorescence-labeled antibodies as to cell surface molecules are mixed with the cells, so that the antibodies are bonded to the cell surface molecules. The fluorescence-labeled antibodies may be antibodies with fluorochromes directly bonded thereto, or may be biotin-labeled antibodies and avidin-bonded fluorochromes bonded by avidin-biotin reaction. Also, the antibodies may be monoclonal antibodies or polyclonal antibodies.

Two or more substances according to the related art may be used in combination for the fluorochromes. Examples include phycoerythrin (PE), FITC, PE-Cy5, PE-Cy7, PE-Texas red, allophycocyanin (APC), APC-Cy7, Ethidium bromide, Propidium iodide (Propidium iodide), Hoechst 33258/33342, DAPI, Acridine orange, Chromomycin, Mithramycin, Olivomycin, Pyronin Y, Thiazole orange, Rhodamine 101 isothiocyanate, BCECF, BCECF-AM, C.SNARF-1, C.SNARF-1-AMA, Aequorin, Indo-1, Indo-1-AM, Fluo-3, Fluo-3-AM, Fura-2, Fura-2-AM, Oxonol, Texas red, Rhodamine 123, 10-N-nony-Acridine orange, Fluorecein, Fluorescein diacetate, Carboxyfluorescein, Caboxyfluorescein diacetate, Carboxydichlorofluorescein, and Carboxydichlorofluorescein diacetate.

Next, light is irradiated on the microparticles multiply-labeled by multiple fluorochromes, and the fluorescence emitted from the excited fluorochromes is received with multiple photodetectors having different input wavelength bands. The measurement procedures can be performed in the same way as with a method using a multi-color measurement flow cytometer according to the related art.

(2) Calculating Procedures (2-1) Approximation Curve

With the calculating procedures, compensation calculation is performed for the detected values from each photodetector that have been obtained in the measuring procedures, and the fluorescence intensity from each fluorochrome is calculated. For the fluorescence intensity compensation method according to an embodiment at this time, the measurement spectrum is approximated by linear sum of the single-stain spectrums obtained from the microparticles single-labeled individually with the fluorochromes, using the restricted least-square method, thereby calculating the true fluorescence intensity from each fluorochrome.

Now, the "measurement spectrum" is obtained by receiving, with photodetectors having different input wavelength bands, fluorescence emitted from fluorochromes excited by irradiating light on microparticles multiply-labeled by multiple fluorochromes with overlapping fluorescence wavelengths, and collecting detected values from the photodetectors. Also, "single-stain spectrum" is the fluorescence wavelength distribution of each fluorochrome, and is obtained by receiving, with a photodetector, fluorescence emitted from a fluorochrome excited by irradiating light on microparticles individually labeled by the fluorochrome, and collecting detected values from the photodetector.

Based on FIG. 1, an approximation curve obtained by approximation of the measurement spectrum from the linear sum of the single-stain spectrums will be described.

In the drawing, the X axis represents observation points, and the Y axis represents detected values. In the drawing, $p_1$ denotes the detected value of fluorescence received at a photodetector 1, $p_2$ denotes the detected value of fluorescence received at a photodetector 2, and $p_n$ denotes the detected value of fluorescence received at a photodetector n. The line connecting the detected values $p_1$ through $p_n$ is the measurement spectrum.

Also, in the drawing, $S_1(i)$ denotes a curve (base function) representing a single-stain spectrum of a first fluorochrome (fluorochrome 1), $S_2(i)$ denotes a curve representing a single-stain spectrum of a second fluorochrome (fluorochrome 2), and $S_M(i)$ denotes a curve representing a single-stain spectrum of an M'th fluorochrome (fluorochrome M). The single-stain spectrums may be obtained by samples individually marked by fluorochromes being prepared each time measurement is performed, or reference spectrums stored in the device beforehand may be used.

At the photodetectors, light is received in a state of the fluorescence from all of the fluorochromes fluorochrome 1 through fluorochrome M leaking in each at a predetermined ratio. Accordingly, the detected value $p_i$ at each photodetector can be approximated by the following expression y(i) as the sum of values obtained by multiplying each base function for the fluorochrome 1 through fluorochrome M by a predetermined ratio. Accordingly, a leakage ratio $x_j$ of fluorescence from each fluorochrome to each photodetector is stipulated by the emission intensity (true fluorescence intensity) of each fluorochrome.

$$p_i \approx y(i) = \sum_{j=1}^{M} S_j(i) \cdot x_j$$

Specifically, the detected value $p_1$ of the photodetector 1 for example, is approximated as a sum y(1) of values of the fluorescence intensity $S_1(1)$ of the fluorochrome 1 multiplied by a ratio $x_1$ through the base function $S_M(1)$ of the fluorochrome M multiplied by a ratio $x_M$. the leakage ratio $x_j$ (j=1 through M) of fluorescence from fluorochromes 1 through M to the photodetector 1 corresponds to the emission intensity of fluorochromes 1 through M.

The approximation curve shown in this expression can be obtained by obtaining $x_j$ with the restricted leas-square method described next. This $x_j$ is equal to the true fluorescence intensity of each fluorochrome, and is a value regarding which a negative value is physically impossible. Accordingly, with the fluorescence intensity compensation method according to an embodiment, compensation calculation is performed with a constriction (lower limit condition) established that this $x_j$ is greater than a predetermined value. By providing a lower limit condition to perform the compensation calculation, the problems of measurement error due to fluorescence intensities from fluorochromes being calculated as negative values, and reduction in populations on the two-dimensional correlation diagram (cytogram), can be solved.

(2-2) Restricted Least-Square Method

The following is a description of a procedure for obtaining $x_j$. First, an evaluation function (chi-squared) shown in Expression (1) below is defined. A parameter $x_j$ (j=1 through M) where this evaluation function satisfies the following Expression (2) and also is the smallest value is obtained $$\chi^2 = \sum_{i=1}^{N} \left( \frac{p_i - \sum_{j=1}^{M} s_{ij} \cdot x_j}{\sigma_i} \right)^2 \quad (1)$$

where $S_{ij}$ represents the detected value $S_j(i)$ of the i'th photodetector in the single-stain spectrum of the j'th fluorochrome, $p_i$ represents the detected value of the i'th photodetector in the measurement spectrum, and $\sigma_i$ represents the inverse number of the weight as to the detected value of the i'th photodetector.

$$x_j \geq U_j \quad (2)$$

where $U_j$ represents the lower limit of the fluorescence intensity of the fluorochrome to be calculated.

The above Expression (2) represents a constriction (lower limit condition) that the fluorescence intensity $x_j$ is greater than the predetermined value ($U_j$).

Now, if we set an N×M order matrix S with $s_{ij}$ as elements, an M order matrix x with $x_j$ as elements, and an n'th order vector p with $p_i$ as elements, obtaining the parameter $x_j$ which satisfies Expression (2) and also gives the smallest value for the evaluation function shown in Expression (1) is the same as solving the following problem.

$$\text{Minimize } \|Sx-p\|_2 \quad (3)$$

$$\text{subject to } Ax \leq b \quad (4)$$

$$x \geq 0 \quad (5)$$

An M×M order matrix A and M×1 order matrix b are set as inequality expressions constricting the fluorescence intensity x to be greater than the predetermined value (U), as shown in the following Expressions (6) and (7).

$$A = \begin{pmatrix} -1 & 0 & \cdots & 0 \\ 0 & -1 & & 0 \\ \vdots & & \ddots & \vdots \\ 0 & 0 & \cdots & -1 \end{pmatrix} \quad (6)$$

$$b = \begin{pmatrix} -U_1 \\ -U_2 \\ \vdots \\ -U_M \end{pmatrix} \quad (7)$$

Squaring and expanding the above Expression (3) yields the following Expression (23).

$$(\|Sx - p\|_2)^2 = (Sx - p)^T (Sx - p) \quad (23)$$
$$= x^T S^T Sx - x^T S^T p - p^T Sx + p^T p$$
$$= x^T (S^T S)x - 2p^T Sx + p^T p$$

The final item $p^T p$ can be ignored to minimize Expression (23). Accordingly, minimizing Expression (23) is equal to minimizing the following Expression (24).

$$\frac{1}{2} x^T (S^T S) x - p^T S x \quad (24)$$

Expression (24) and the above Expressions (4) and (5) are referred to as quadratic programming problems. A "quadratic programming problem" is a problem wherein, with D as an n×n order positive semidefinite symmetric matrix, c as an n'th order vector, A as an m×n order matrix, and b as an m'th order vector, of the n'th order vectors satisfying the linear constraint "Ax≤b, x≤0", that in which the target function "f(x)=$x^T$Ax/2+$c^T$x" given in quadratic form is smallest is obtained. The following Expressions (25) through (27) illustrate a quadratic programming problem. A quadratic programming problem is a particular kind of nonlinear programming program where a strict optimal solution is obtained by a finite number of repetitions.

$$\text{Minimize } \frac{1}{2} x^T D x + c^T x \quad (25)$$

$$\text{subject to } Ax \leq b \quad (26)$$

$$x \geq 0 \quad (27)$$

The above Expressions (24), (4), and (5), are equivalent to replacing D and c in Expression (25) as shown below and replacing A and b in Expression (26) as shown in Expressions (6) and (7) to solve the quadratic programming problem.

$$D = S^T S \quad (28)$$

$$c = -(p^T S)^T = -S^T p \quad (29)$$

(2-3) Constrictions (Lower Limit Conditions)

(2-3-1) Average Value as Lower Limit Condition (First Embodiment and Modification Thereof)

For the lower limit $U_j$ (j=1 through M) to use as a constraint for solving the quadratic programming problem in the following Expressions (3) through (5), an appropriate value is set as a smallest detection value of the j'th fluorochrome, assuming that an undyed microparticle which has not been marked by a fluorochrome was been measured. Specifically, for the lower limit $U_j$, an undyed average value $V_j$ of the j'th fluorochrome obtained from the average value of detection values from each photodetector, obtained by irradiating light on microparticles not marked with the j'th fluorochrome, can be used. For the undyed average value $V_j$, the average value of detection values at the photodetector at which the single-stain spectrum of the j'th fluorochrome exhibits the greatest detection values is used, for example. Alternatively, the detection average value of the photodetector exhibiting the greatest detection values and the detection average values of the photodetectors before and after that photodetector (e.g., the (j−1)'th and (j+1)'th photodetectors) may further be averaged to be used as the undyed average value $V_j$, or the like.

$$\text{Minimize } \|Sx - p\|_2 \quad (3)$$

$$\text{subject to } Ax \leq b \quad (4)$$

$$x \geq 0 \quad (5)$$

-continued $$A = \begin{pmatrix} -1 & 0 & \cdots & 0 \\ 0 & -1 & & 0 \\ \vdots & & \ddots & \vdots \\ 0 & 0 & \cdots & -1 \end{pmatrix} \quad (6)$$

$$b = \begin{pmatrix} -U_1 \\ -U_2 \\ \vdots \\ -U_M \end{pmatrix} \quad (7)$$

As a modification, the quadratic programming method with no linear constraints of Expression (4) above can be applied. In this case, the aforementioned parameter $x_j$ (j=1 through M) can be obtained by solving the quadratic programming problem of Expressions (12) and (13) below, and executing the following Expression (14)

Minimize $\|Sx'-(p-u)\|_2$ (12)

subject to $x'\geq 0$ (13)

$x=x'+U$ (14)

where S represents an N×M order matrix with $s_{ij}$ as elements, x represents an M order matrix with $x_j$ as elements, p represents an N'th order vector with $p_i$ as elements, u represents an N'th order vector with the average value $v_i$ of detected values from the i'th photodetector, obtained by irradiating light on microparticles unmarked with the j'th fluorochrome, as elements, and U represents an M'th order vector with the undyed average value $V_j$ of the j'th fluorochrome obtained from the average value $v_i$ as elements. For the undyed average value $V_j$, the average value of detection values at the photodetector at which the single-stain spectrum of the j'th fluorochrome exhibits the greatest detection values is used, for example. Alternatively, the detection average value of the photodetector exhibiting the greatest detection values and the detection average values of the photodetectors before and after that photodetector (e.g., the (j−1)'th and (j+1)'th photodetectors) may further be averaged to be used as the undyed average value $V_j$, or the like.

(2-3-2) Random Number Following Probability Density Function as Lower Limit Condition (Second Embodiment and Modification Thereof)

For the lower limit $U_j$ (j=1 through M) to use as a constraint for solving the quadratic programming problem in Expressions (3) through (5), a random number generated following an undyed probability density function $F_j(U_j)$ of the j'th fluorochrome obtained from a probability density function of detection values from each photodetector, obtained by irradiating light on microparticles not marked with the j'th fluorochrome, can be used. For the undyed probability density function $F_j(U_j)$, the probability density function at the photodetector at which the single-stain spectrum of the j'th fluorochrome exhibits the greatest detection values is used, for example. Alternatively, a function calculated from the probability density function of the photodetector exhibiting the greatest detection values and the probability density functions of the photodetectors before and after that photodetector (e.g., the (j−1)'th and (j+1)'th photodetectors) may be used as the undyed probability density function $F_j(U_j)$, or the like.

As a modification, in the event of applying the quadratic programming problem with no linear constraints of Expression (4) above, the aforementioned parameter $x_j$ (j=1 through M) can be obtained by solving the quadratic programming problem of Expressions (15) and (16) below, and executing the following Expression (17)

Minimize $\|Sx'-(p-u)\|_2$ (15)

subject to $x'\geq 0$ (16)

$x=x'+U$ (17)

where S represents an N×M order matrix with $s_{ij}$ as elements, x represents an M order matrix with $x_j$ as elements, p represents an N'th order vector with $p_i$ as elements, u represents an N'th order vector with the random numbers $u_i$ generated following the probability density function $f_i(u_i)$ of the detection values of the i'th photodetector, obtained by irradiating light on microparticles unmarked with the j'th fluorochrome, as elements, and U represents an M'th order vector with the random numbers $U_j$ generated following the undyed probability density function $F_j(U_j)$ of the j'th fluorochrome obtained from the probability density function $f_i(u_i)$ as elements. For the undyed probability density function $F_j(U_j)$, the probability density function $f_i(u_i)$ of detection values at the photodetector at which the single-stain spectrum of the j'th fluorochrome exhibits the greatest detection values is used, for example. Alternatively, a function calculated from the probability density function of the photodetector exhibiting the greatest detection values and the probability density functions of the photodetectors before and after that photodetector (e.g., the (j−1)'th and (j+1)'th photodetectors) may be used as the probability density function $F_j(U_j)$, or the like.

(2-3-3) Random Number Following Normal Distribution as Lower Limit Condition (Third Embodiment and Modification Thereof)

Further, for the lower limit $U_j$ (j=1 through M) to use as a constraint for solving the quadratic programming problem in Expressions (3) through (5), a random number generated by obtaining the undyed average value $V_j$ and undyed standard deviation $\rho_j$ of the of the j'th fluorochrome from the average value and dispersion of detection values from each photodetector, obtained by irradiating light on microparticles not marked with the j'th fluorochrome, and generating the random number following the probability density function $F_j(U_j)$ in the following Expression (9) as the aforementioned lower limit value $U_j$, can be used. This random number will be a random number following normal distribution (normal random number). For the undyed average value $V_j$ and undyed standard deviation $\rho_j$, the average value and standard deviation at the photodetector at which the single-stain spectrum of the j'th fluorochrome exhibits the greatest detection values is used, for example. Alternatively, a value calculated from the average value and standard deviation of the photodetector exhibiting the greatest detection values and the average values and standard deviation of the photodetectors before and after that photodetector (e.g., the (j−1)'th and (j+1)'th photodetectors) may be used as the undyed average value $V_j$ and undyed standard deviation $\rho_j$, or the like.

$$F_j(U_j) = \frac{1}{\sqrt{2\pi}\,\rho_j} e^{-\frac{(U_j-V_j)^2}{2\rho_j^2}}. \quad (9)$$

As a modification, in the event of applying the quadratic programming problem with no linear constraints of Expression (4) above, the aforementioned parameter $x_j$ (j=1 through M) can be obtained by solving the quadratic programming problem of Expressions (20) and (21) below, and executing the following Expression (22)

$$f_i(u_i) = \frac{1}{\sqrt{2\pi}\,\sigma_i} e^{-\frac{(U_i-V_i)^2}{2\sigma_i^2}} \tag{18}$$

$$F_j(U_j) = \frac{1}{\sqrt{2\pi}\,\rho_j} e^{-\frac{(U_j-V_j)^2}{2\rho_j^2}} \tag{19}$$

Minimize $\|Sx' - (p - u)\|_2$ (20)

subject to $x' \geq 0$ (21)

$x = x' + U$ (22)

where S represents an N×M order matrix with $s_{ij}$ as elements, x represents an M order matrix with $x_j$ as elements, p represents an N'th order vector with $p_i$ as elements, u represents an N'th order vector with a random number $u_j$ generated by obtaining the average value $V_j$ and dispersion $\sigma_i$ of the of the j'th fluorochrome obtained by irradiating light on microparticles not marked with the j'th fluorochrome, and generating the random number $u_j$ following the probability density function $f_j(u_j)$ in Expression (18), as the elements, and U represents an M'th order vector having as the elements a random number $U_j$ generated by obtaining the undyed average value $V_j$ and undyed standard deviation $\rho_j$ from the average value $v_i$ and dispersion $\sigma_i$ and generating the random number $U_j$ following the probability density function $F_j(U_j)$ in Expression (19). For the undyed average value $V_j$ and undyed standard deviation $\rho_j$, the average value i and standard deviation of detection values at the photodetector at which the single-stain spectrum of the j'th fluorochrome exhibits the greatest detection values is used, for example. Alternatively, a value calculated from the average value and standard deviation of the photodetector exhibiting the greatest detection values and the average values and standard deviation of the photodetectors before and after that photodetector (e.g., the (j−1)'th and (j+1)'th photodetectors) may be used as the undyed average value V, and undyed standard deviation $\rho_j$, or the like.

(2-3-4) 0 as Lower Limit Condition (Fourth Embodiment)

In the event of applying the quadratic programming method with no linear constraints of Expression (4) above, by setting the lower limit value to 0, the aforementioned parameter $x_j$ (j=1 through M) can be obtained by solving the quadratic programming problem of Expressions (10) and (11) below Minimize $\|Sx-p\|_2$ (10)

subject to $x \geq 0$ (11)

where S represents an N×M order matrix with $s_{ij}$ as elements, x represents an M order matrix with $x_j$ as elements, and p represents an N'th order vector with $p_i$ as elements.

2. Fluorescence Intensity Calculating Device

The fluorescence intensity calculation device according to an embodiment is configured of a fluid system, an optical system, a sorting system, a data processing system, and so forth, in the same way as with a flow cytometer according to the related art.

The fluid system is an arrangement for flowing a sample liquid including microparticles to be measured at a flow cell so as to flow at the center of a laminated flow of a sheath solution, such that the microparticles are arrayed in a single row in the flow cell. The microparticles may be arrayed in a single row in a channel formed on a microchip, instead of a flow cell.

The optical system is an arrangement to receive, with photodetectors, fluorescence emitted from fluorochromes excited by light being emitted on microparticles marked by the fluorochromes, and collect detected values from each of the photodetectors to obtain a measurement spectrum. Forward-scattered light and side-scatter light from the microparticles, and further scattered light such as Rayleigh scattering and Mie scattering and so forth, is detected with the optical system. The optical system is more specifically configured of an irradiation system made up of a laser light source, condenser lenses, dichroic mirrors, band-pass filters, and so forth, to collect the laser beam and irradiate onto the microparticles, and a detecting system for detecting fluorescence and scattered light emitted from the microparticles due to irradiation of the laser beam. The detecting system is configured of, for example, PMTs (Photo Multiplier Tubes) or area imaging devices such as CCD or CMOS devices or the like, with multiple photodetectors of different input wavelength bands being disposed.

In the event of sorting microparticles, a sample solution is discharged in space outside of a flow cell as droplets including the microparticles, and the direction of movement of the droplets is controlled so as to sort microparticles having desired properties. The sorting system is configured of a vibrating element such as a piezo device or the like for discharging the sample solution from the flow cell in droplets, a charging unit providing the discharged droplets with a charge, counter electrodes disposed following the direction of motion of the droplets, facing one another across space where the moving droplets exist, and so forth.

The data processing system inputs detected values form the photodetectors as electric signals, and analyzes the optical properties of the microparticles based on the electric signals. The data processing system approximates the measurement spectrum obtained by collecting detected values form the photodetectors by linear sum of single-stain spectrums following the above-described method, and calculates the true fluorescence intensity emitted from each fluorochrome. Accordingly, the data processing system has a storage medium such as a hard disk or the like for storing a program for executing the above-described fluorescence intensity calculation method according to an embodiment, and a CPU and memory and the like for executing the program.

In order to improve quality of signals from each photodetector, the data processing system preferably is provided with a noise filter for smoothing the data between each of the photodetectors. Smoothing processing is performed taking into consideration the number of photodetectors, the input wavelength band, the fluorochromes used, the autofluorescence wavelength of the microparticles to be measured, and further the noise frequency component of the devices, and so forth. Performing data smoothing enables the effects of noise to be suppressed, calculation precision improved, and the fluorescence intensity can be calculated more accurately.

A 32-channel multicolor measurement flow cytometer was used with virtual output data to compare computation results of a fluorescence compensation method according to the related art using a compensation matrix with the fluorescence compensation method according to an embodiment using the restricted leas-square method.

Used for the fluorochromes were FITC (CH5), Alexa 500 (CH6), Alexa 514 (CH10), Alexa 532 (CH12), PE (CH15), PE-TR (CH19), PI (CH21), Alexa 600 (CH20), PE-Cy5 (CH24), PerCP (CH25), PerCP-Cy5.5 (CH26), and PE-Cy7 (CH31). The channels Nos. in the parentheses indicate the assignment of channels as to the fluorochromes in the method according to the related art using the compensation matrix.

Figure 2:
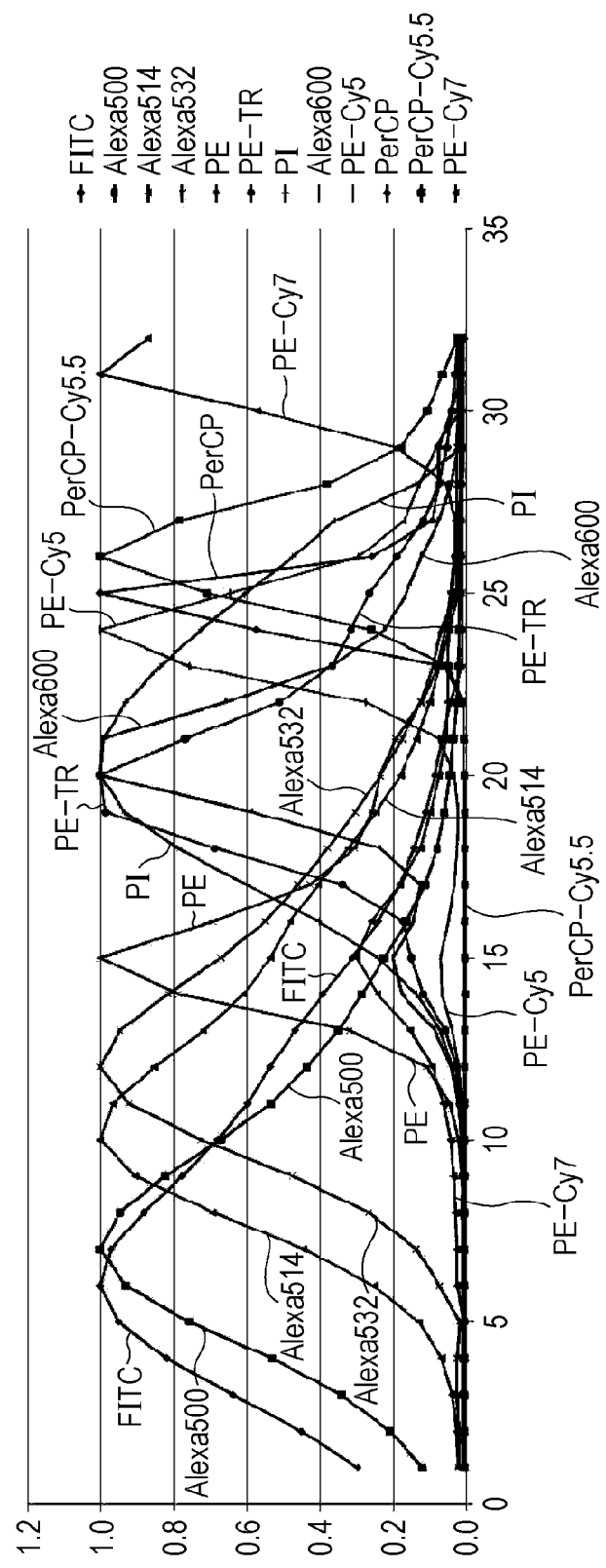
FIG. 2 is a graph illustrating single-stain spectrums of fluorochromes used in an embodiment.

FIG. 2 shows single-stain spectrums of each of the fluorochromes. Simulation data with these single-stain spectrums each emerging at random intensities in an exclusive manner, with detector and electrical noise further virtually added to each detected data, was generated by the Monte Carlo method. Typical analysis results obtained by performing fluorescence compensation of the generated simulation data using the single-stain spectrums shown in FIG. 2 and the method according to the related art and the method according to an embodiment, are shown below.

Figure 3:
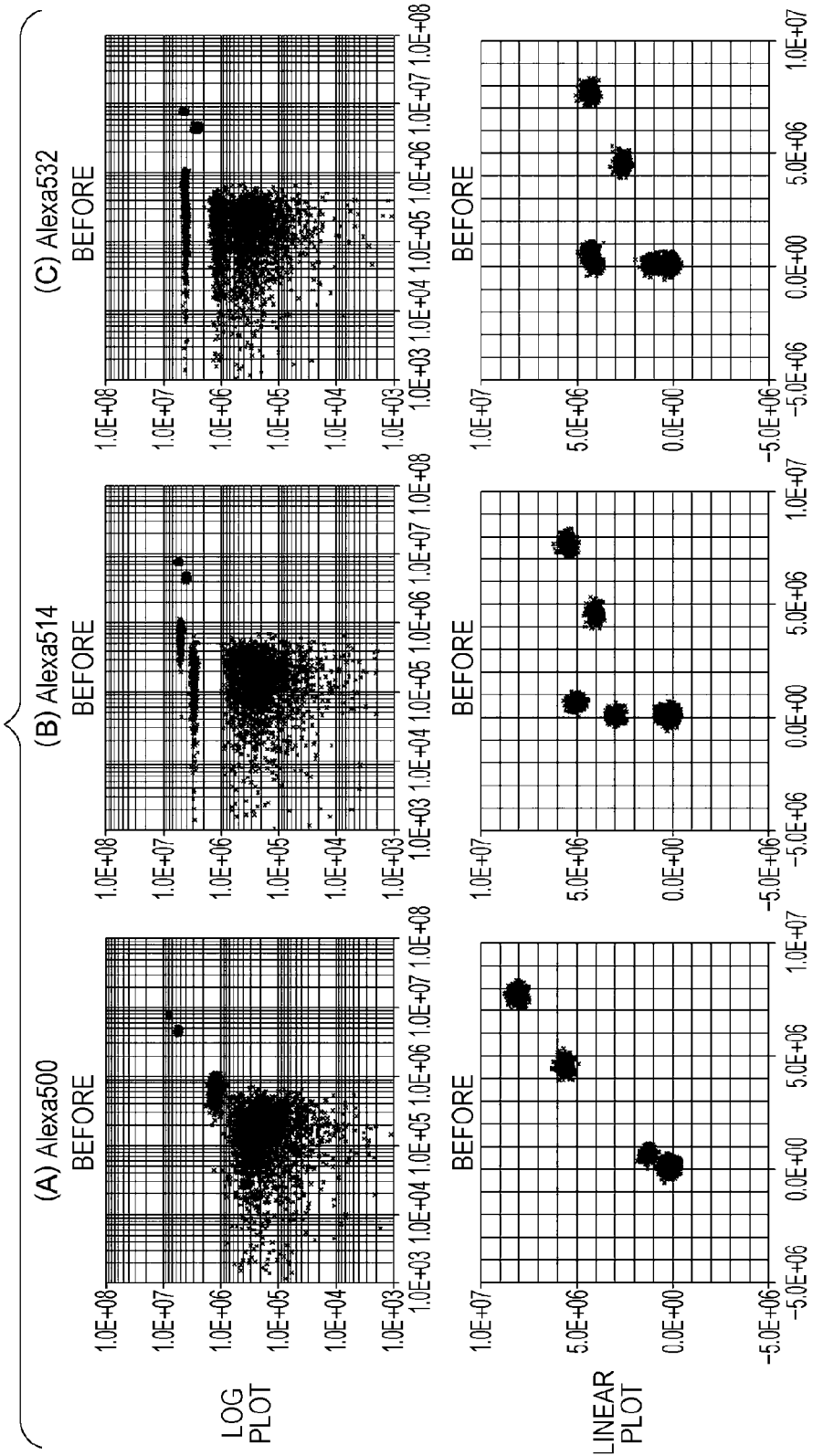
FIG. 3 is a two-dimensional correlation diagram created from virtual output data with no fluorescence compensation performed.

FIG. 3 shows two-dimensional correlation diagrams created from virtual output data without performing fluorescence compensation. The vertical axes of (A) through (C) indicate the fluorescence intensity of Alexa 500, Alexa 514, and Alexa 532, respectively, and the horizontal axis indicates the fluorescence intensity of FITC. The upper tier is long-scale plotted two-dimensional correlation diagrams, and the lower tier is linear-scale plotted two-dimensional correlation diagrams (the same for FIGS. 4 through 11 hereinafter).

Figure 4:
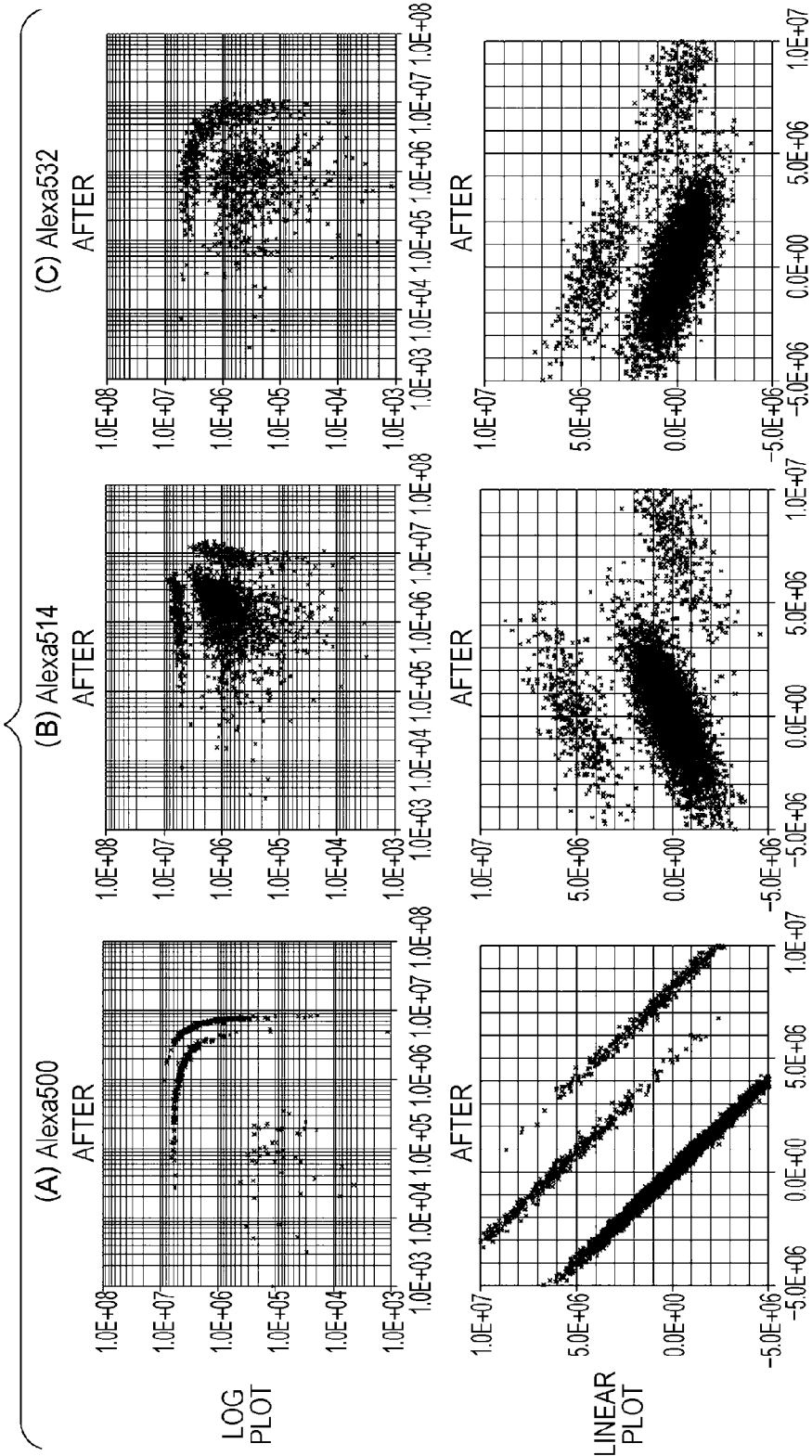
FIG. 4 is a two-dimensional correlation diagram created with virtual output data subjected to fluorescence compensation using a compensation matrix (comparative example)

FIG. 4 shows two-dimensional correlation diagrams created from virtual output data with fluorescence compensation performed using a compensation matrix for comparison. In the linear-scale plotted two-dimensional correlation diagrams, there are sub-populations where the fluorescence intensity of FITC and Alexa 500, Alexa 514, and Alexa 532 is calculated as a negative value. Accordingly, the populations plotted on long-scale two-dimensional correlation diagrams are markedly decreased as compared to the populations plotted on the linear scale two-dimensional correlation diagrams.

Figure 5:
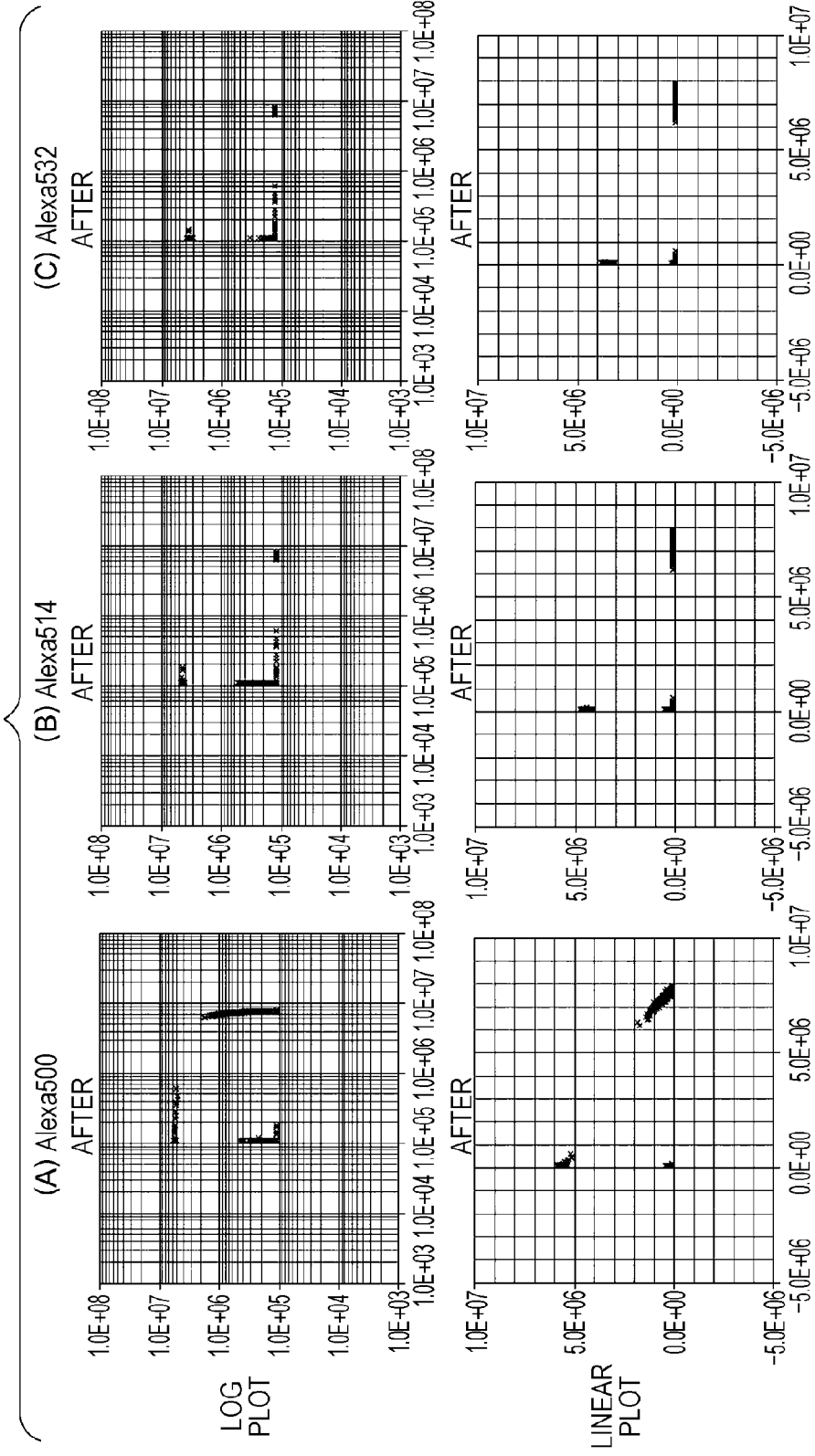
FIG. 5 is a two-dimensional correlation diagram created with virtual output data subjected to fluorescence compensation by way of a method according to a first embodiment, where the average value is taken as the lower limit.

FIG. 5 shows two-dimensional correlation diagrams created from virtual output data with fluorescence compensation performed by the method according to the first embodiment where the lower value is the average value. In the linear-scale plotted two-dimensional correlation diagrams, the fluorescence intensity of FITC and Alexa 500, Alexa 514, and Alexa 532 is calculated as a positive value. Accordingly, the populations plotted on the linear scale two-dimensional correlation diagrams are all plotted on the long-scale two-dimensional correlation diagrams as well.

Figure 6:
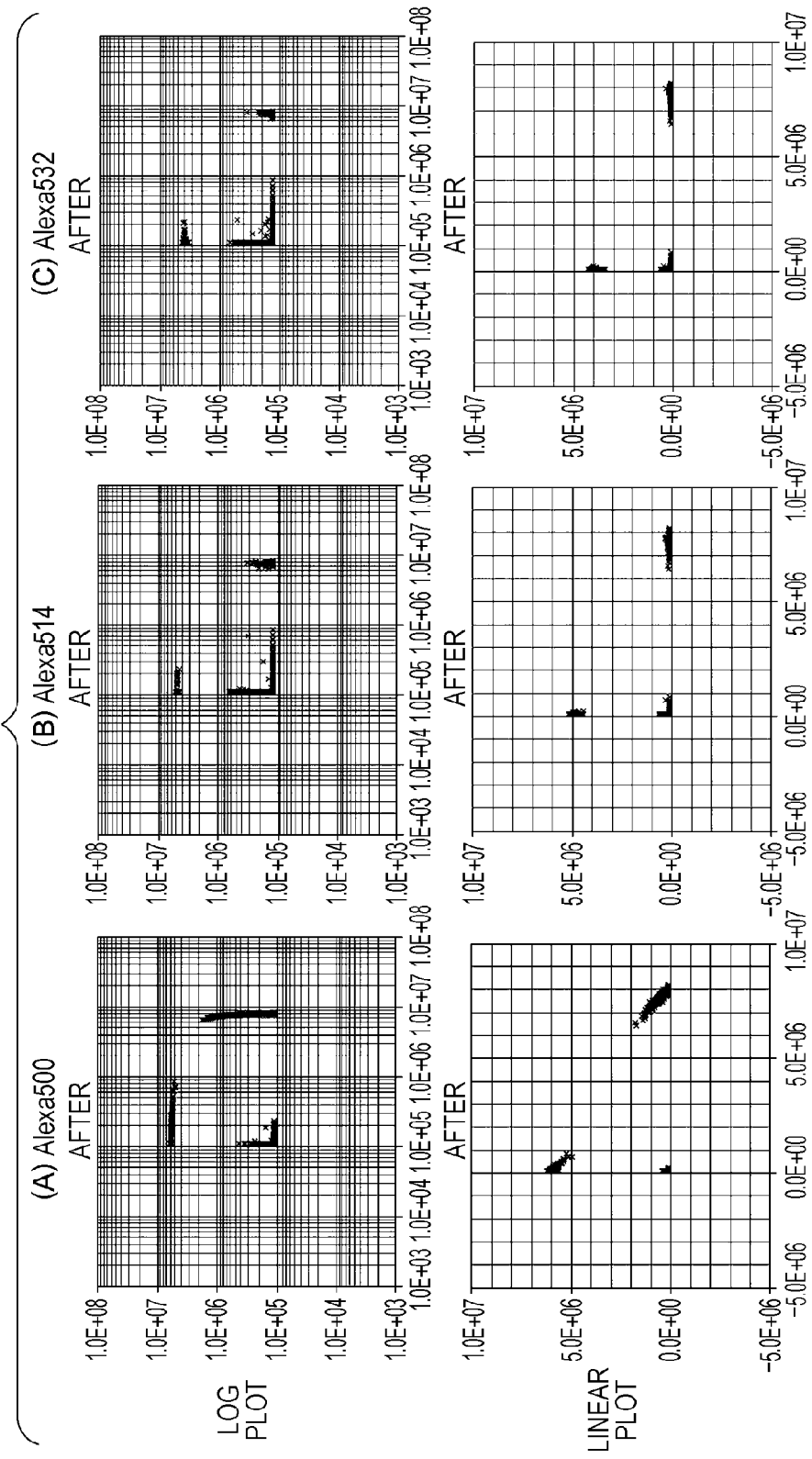
FIG. 6 is a two-dimensional correlation diagram created with virtual output data subjected to fluorescence compensation by way of a method according to a modification of the first embodiment, where the average value is taken as the lower limit, with no linear constraints.

FIG. 6 is a two-dimensional correlation diagram created with virtual output data subjected to fluorescence compensation by the method according to a modification of the first embodiment, where the average value is taken as the lower limit, with no linear constraints.

Figure 7:
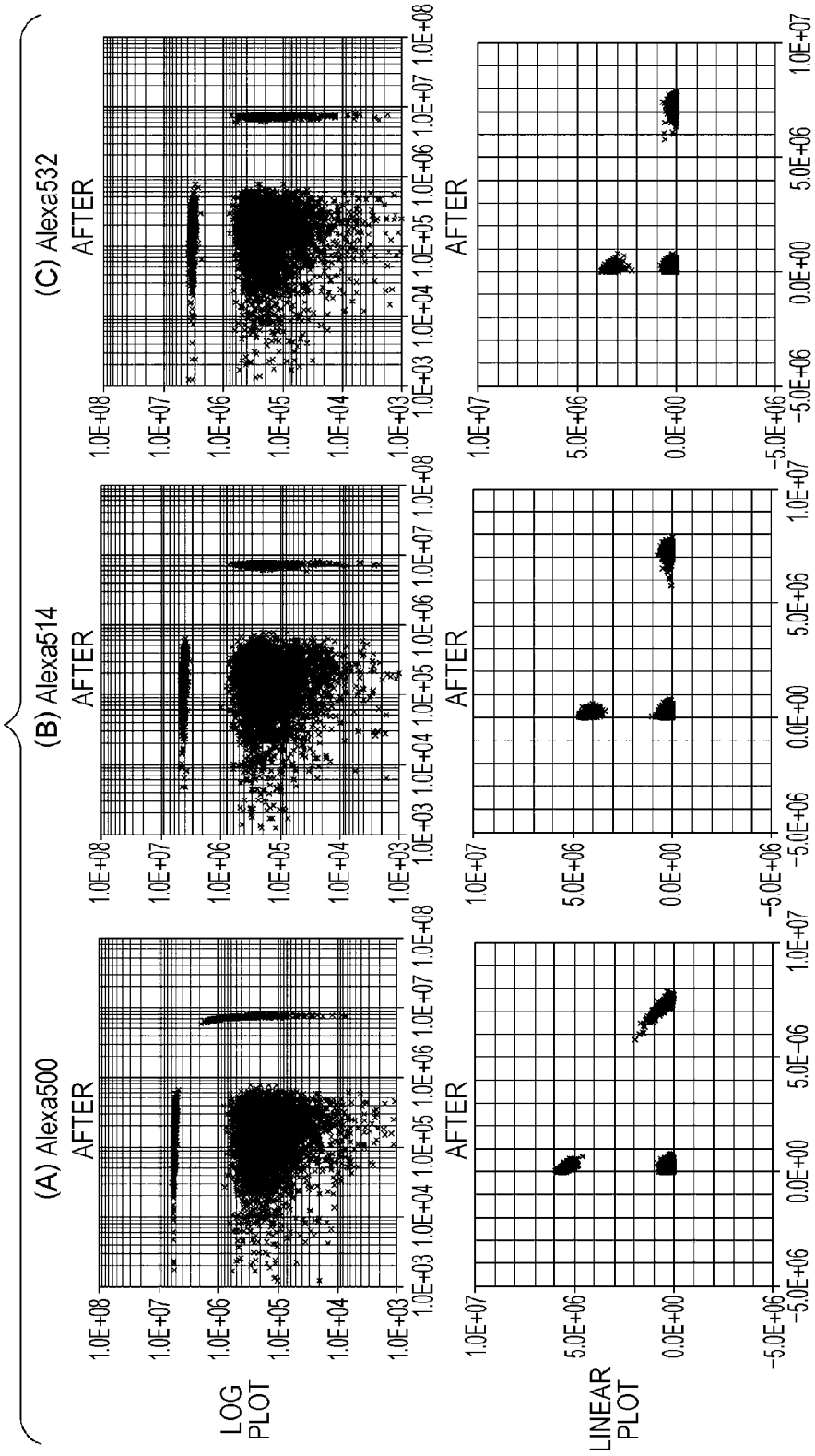
FIG. 7 is a two-dimensional correlation diagram created with virtual output data subjected to fluorescence compensation by way of a method according to a second embodiment, where the lower limit is a random number following a probability density function.

FIG. 7 is a two-dimensional correlation diagram created with virtual output data subjected to fluorescence compensation by the method according to the second embodiment, where the lower limit is a random number following a probability density function.

Figure 8:
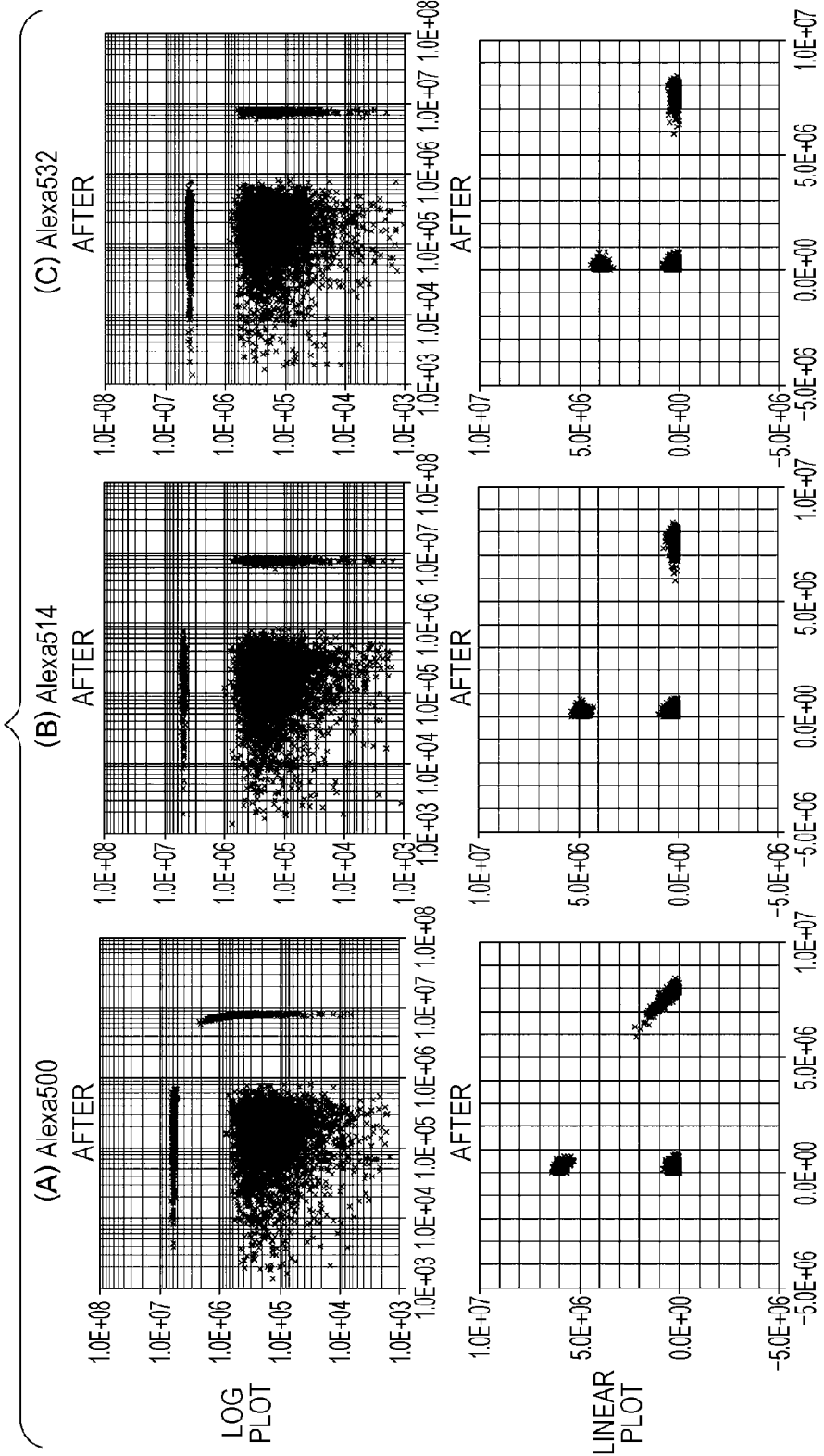
FIG. 8 is a two-dimensional correlation diagram created with virtual output data subjected to fluorescence compensation by way of a method according to a modification of the second embodiment, where the lower limit is a random number following a probability density function, with no linear constraints.

FIG. 8 is a two-dimensional correlation diagram created with virtual output data subjected to fluorescence compensation by the method according to a modification of the second embodiment, where the lower limit is a random number following a probability density function, with no linear constraints.

Figure 9:
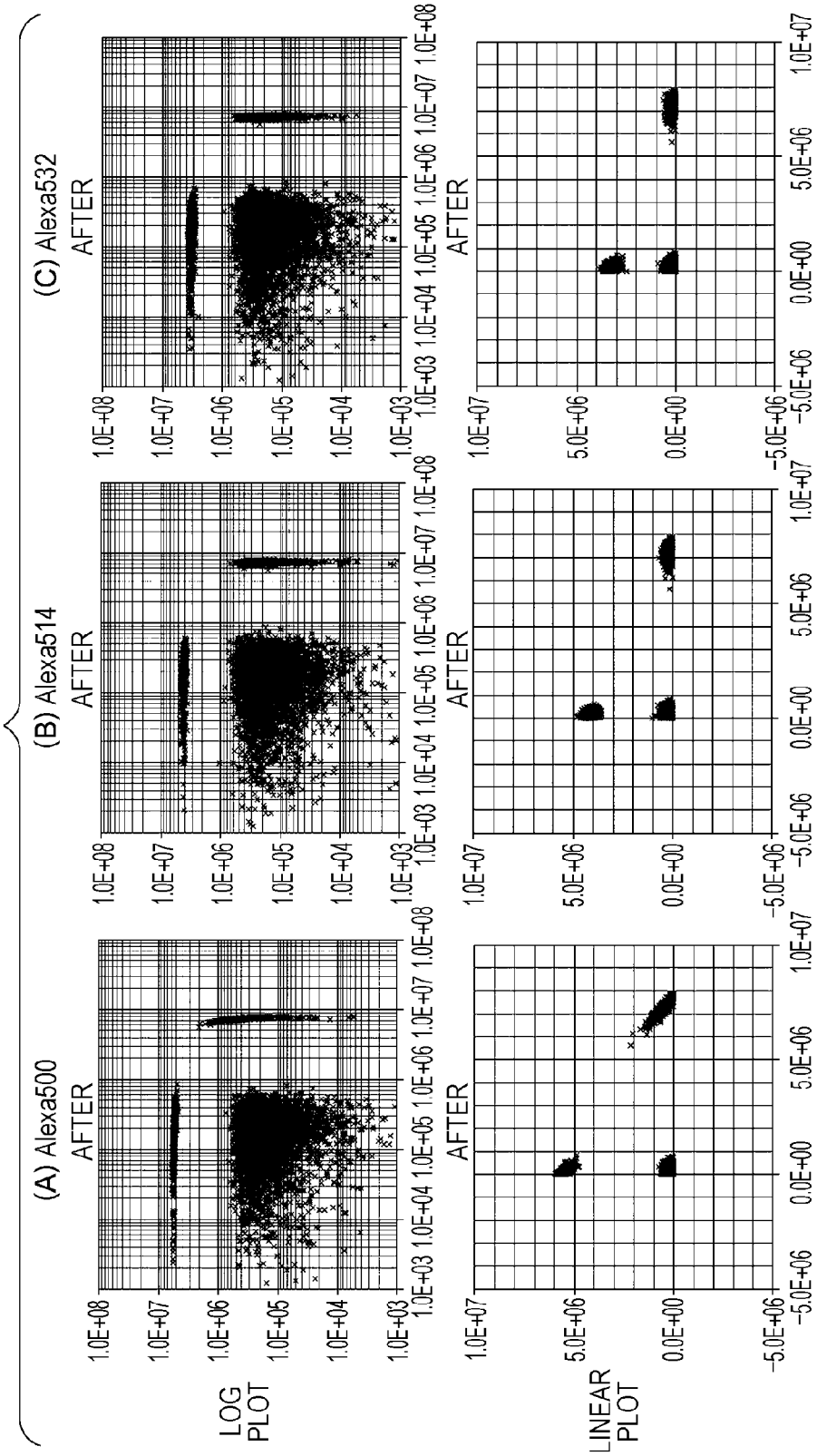
FIG. 9 is a two-dimensional correlation diagram created with virtual output data subjected to fluorescence compensation by way of a method according to a third embodiment, where the lower limit is a normal random number.

FIG. 9 is a two-dimensional correlation diagram created with virtual output data subjected to fluorescence compensation by the method according to the third embodiment, where the lower limit is a normal random number.

Figure 10:
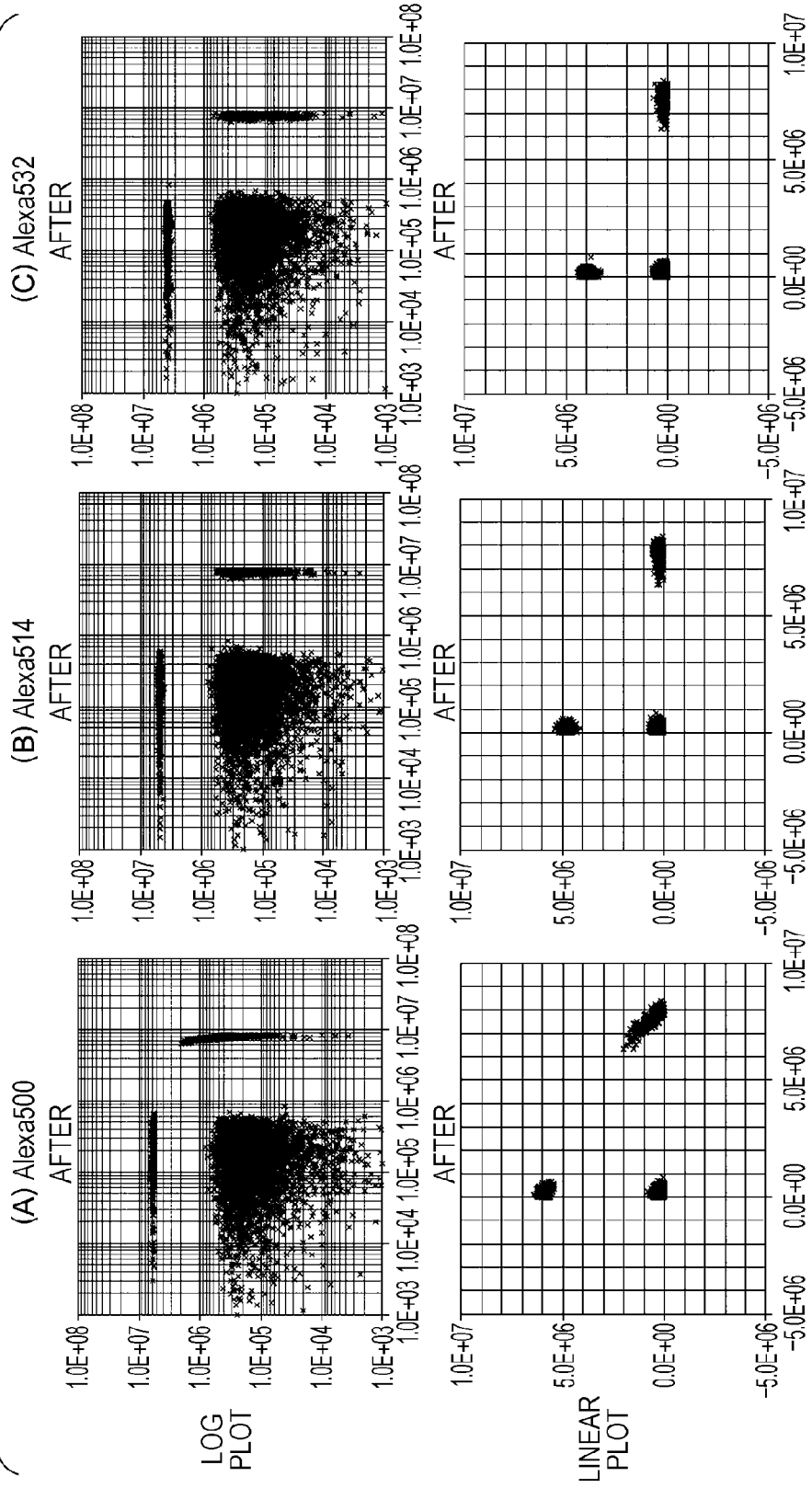
FIG. 10 is a two-dimensional correlation diagram created with virtual output data subjected to fluorescence compensation by way of a method according to a modification of the third embodiment, where the lower limit is a normal random number, with no linear constraints.

FIG. 10 is a two-dimensional correlation diagram created with virtual output data subjected to fluorescence compensation by the method according to a modification of the third embodiment, where the lower limit is a normal random number, with no linear constraints.

Figure 11:
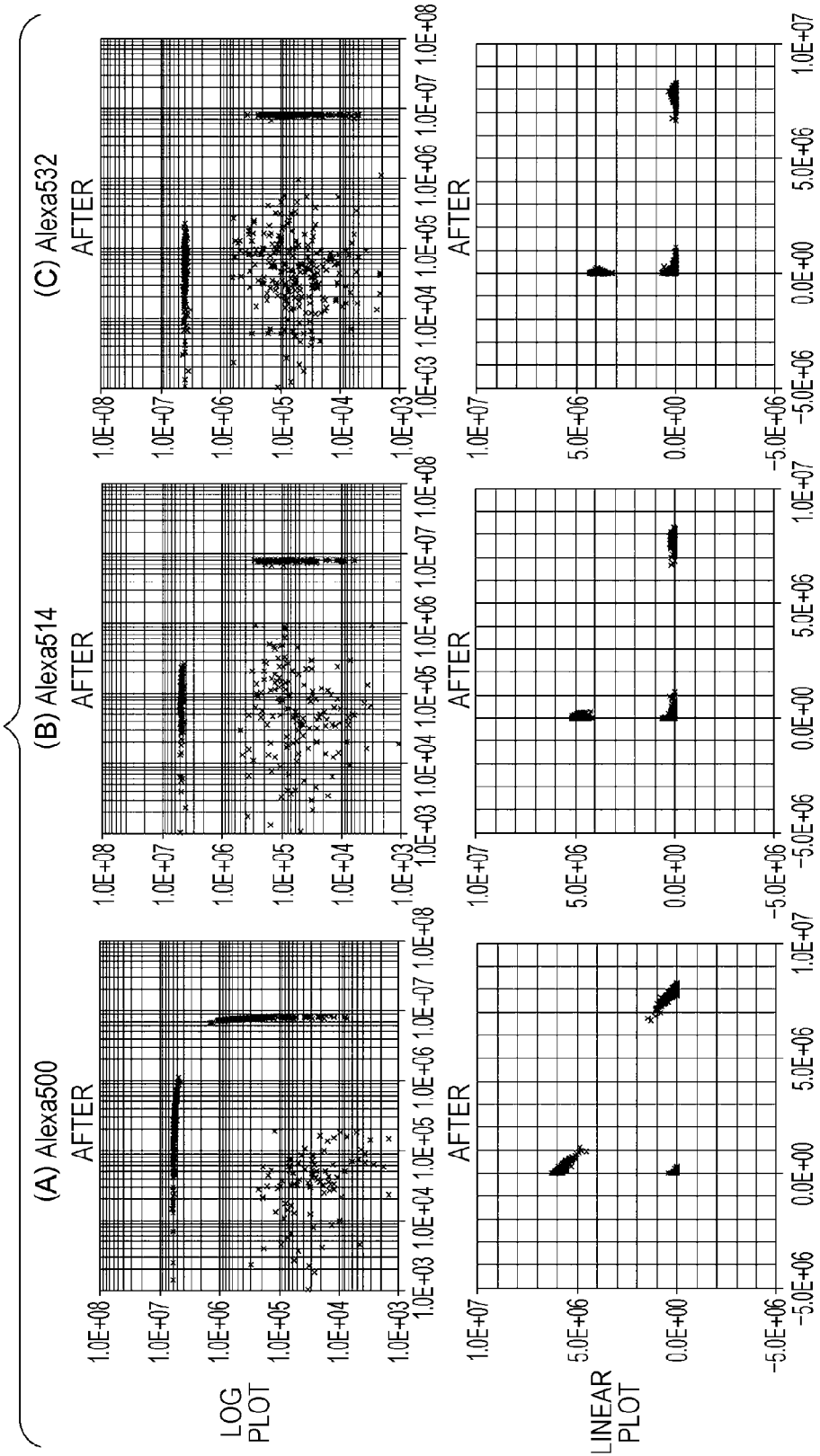
FIG. 11 is a two-dimensional correlation diagram created with virtual output data subjected to fluorescence compensation by way of a method according to a fourth embodiment, where the lower limit is 0.

FIG. 11 is a two-dimensional correlation diagram created with virtual output data subjected to fluorescence compensation by the method according to the fourth embodiment, where the lower limit is 0.

With FIGS. 6 through 11 as well, the fluorescence intensity of FITC and Alexa 500, Alexa 514, and Alexa 532, is calculated as a positive value. Accordingly, the populations plotted on the linear scale two-dimensional correlation diagrams are all plotted on the long-scale two-dimensional correlation diagrams as well.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The application is claimed as follows:

1. A fluorescence intensity compensation method, comprising:
   receiving, with photodetectors having different input wavelength bands, fluorescence emitted from fluorochromes excited by irradiating light on microparticles multiply-labeled by a plurality of fluorochromes with overlapping fluorescence wavelengths;
   collecting detected values for the photodetectors; and
   obtaining a measurement spectrum, by approximating, from a linear sum of single-stain spectrums obtained from microparticles individually labeled with the fluorochromes;
   wherein approximation of said measurement spectrum by the linear sum of said single-stain spectrums is performed using a restricted least-square method;
   wherein the intensity of fluorescence emitted from each fluorochrome is calculated by obtaining a parameter $x_j$ (j=1 through M) where an evaluation function shown in the following Expression (1) satisfies the following Expression (2) and also is a smallest value $$\chi^2 = \sum_{i=1}^{N} \left( \frac{p_i - \sum_{j=1}^{M} s_{ij} \cdot x_j}{\sigma_i} \right)^2 \quad (1)$$

$$x_j \geq U_j \quad (2)$$

where $S_{ij}$ represents a detected value of the i'th photodetector in the single-stain spectrum of the j'th fluorochrome, $p_i$ represents a detected value of the i'th photodetector in the measurement spectrum, $\sigma_i$ represents an inverse number of a weight as to a detected value of the i'th photodetector, and $U_j$ represents a lower limit value of the fluorescence intensity of each fluorochrome to be calculated;
   wherein said parameter $x_j$ (j=1 through M) is obtained by solving the quadratic programming problem in the following Expressions (3) through (5)

$$\text{Minimize } \|Sx - p\|_2 \quad (3)$$

$$\text{subject to } Ax \leq b \quad (4)$$

$$x \geq 0 \quad (5)$$

$$A = \begin{pmatrix} -1 & 0 & \cdots & 0 \\ 0 & -1 & & 0 \\ \vdots & & \ddots & \vdots \\ 0 & 0 & \cdots & -1 \end{pmatrix} \quad (6)$$

-continued $$b = \begin{pmatrix} -U_1 \\ -U_2 \\ \vdots \\ -U_M \end{pmatrix} \quad (7)$$

where S represents an N×M order matrix with $s_{ij}$ as elements, x represents an M order matrix with $x_j$ as elements, p represents an N'th order vector with $p_i$ as elements, A is set as an M×M order matrix and b as an M×1 order matrix, and $U_1$ through $U_M$ represent said lower limit value;

wherein in said Expression (2), an undyed average value $V_j$ of the j'th fluorochrome obtained from an average value of detection values from each of said photodetectors, obtained by irradiating light on microparticles not marked with the j'th fluorochrome, is used as said lower limit value $U_j$.

2. A fluorescence intensity compensation method, comprising:

receiving, with photodetectors having different input wavelength bands, fluorescence emitted from fluorochromes excited by irradiating light on microparticles multiply-labeled by a plurality of fluorochromes with overlapping fluorescence wavelengths;

collecting detected values for the photodetectors; and obtaining a measurement spectrum, by approximating, from a linear sum of single-stain spectrums obtained from microparticles individually labeled with the fluorochromes;

wherein approximation of said measurement spectrum by the linear sum of said single-stain spectrums is performed using a restricted least-square method;

wherein the intensity of fluorescence emitted from each fluorochrome is calculated by obtaining a parameter $x_j$ (j=1 through M) where an evaluation function shown in the following Expression (1) satisfies the following Expression (2) and also is a smallest value $$\chi^2 = \sum_{i=1}^{N} \left( \frac{p_i - \sum_{j=1}^{M} s_{ij} \cdot x_j}{\sigma_i} \right)^2 \quad (1)$$

$$x_j \geq U_j \quad (2)$$

where $S_{ij}$ represents a detected value of the i'th photodetector in the single-stain spectrum of the j'th fluorochrome, $p_i$ represents a detected value of the i'th photodetector in the measurement spectrum, $\sigma_i$ represents an inverse number of a weight as to a detected value of the i'th photodetector, and $U_j$ represents a lower limit value of the fluorescence intensity of each fluorochrome to be calculated;

wherein said parameter $x_j$ (j=1 through M) is obtained by solving the quadratic programming problem in the following Expressions (3) through (5)

Minimize $\|Sx - p\|_2$ (3)

subject to $Ax \leq b$ (4)

$x \geq 0$ (5)

$$A = \begin{pmatrix} -1 & 0 & \cdots & 0 \\ 0 & -1 & & 0 \\ \vdots & & \ddots & \vdots \\ 0 & 0 & \cdots & -1 \end{pmatrix} \quad (6)$$

$$b = \begin{pmatrix} -U_1 \\ -U_2 \\ \vdots \\ -U_M \end{pmatrix} \quad (7)$$

where S represents an N×M order matrix with $s_{ij}$ as elements, x represents an M order matrix with $x_j$ as elements, p represents an N'th order vector with $p_i$ as elements, A is set as an M×M order matrix and b as an M×1 order matrix, and $U_1$ through $U_M$ represent said lower limit value;

wherein in said Expression (2), a random number generated following an undyed probability density function $F_j(U_j)$ of the j'th fluorochrome obtained from a probability density function of detection values from each of said photodetectors, obtained by irradiating light on microparticles not marked with the j'th fluorochrome, is used as said lower limit value $U_j$.

3. A fluorescence intensity compensation method, comprising:

receiving, with photodetectors having different input wavelength bands, fluorescence emitted from fluorochromes excited by irradiating light on microparticles multiply-labeled by a plurality of fluorochromes with overlapping fluorescence wavelengths;

collecting detected values for the photodetectors; and obtaining a measurement spectrum, by approximating, from a linear sum of single-stain spectrums obtained from microparticles individually labeled with the fluorochromes;

wherein approximation of said measurement spectrum by the linear sum of said single-stain spectrums is performed using a restricted least-square method;

wherein the intensity of fluorescence emitted from each fluorochrome is calculated by obtaining a parameter $x_j$ (j=1 through M) where an evaluation function shown in the following Expression (1) satisfies the following Expression (2) and also is a smallest value $$\chi^2 = \sum_{i=1}^{N} \left( \frac{p_i - \sum_{j=1}^{M} s_{ij} \cdot x_j}{\sigma_i} \right)^2 \quad (1)$$

$$x_j \geq U_j \quad (2)$$

where $S_{ij}$ represents a detected value of the i'th photodetector in the single-stain spectrum of the j'th fluorochrome, $p_i$ represents a detected value of the i'th photodetector in the measurement spectrum, $\sigma_i$ represents an inverse number of a weight as to a detected value of the i'th photodetector, and $U_j$ represents a lower limit value of the fluorescence intensity of each fluorochrome to be calculated;

wherein said parameter $x_j$ (j=1 through M) is obtained by solving the quadratic programming problem in the following Expressions (3) through (5)

$$\text{Minimize } \|Sx - p\|_2 \quad (3)$$

$$\text{subject to } Ax \leq b \quad (4)$$

$$x \geq 0 \quad (5)$$

$$A = \begin{pmatrix} -1 & 0 & \cdots & 0 \\ 0 & -1 & & 0 \\ \vdots & & \ddots & \vdots \\ 0 & 0 & \cdots & -1 \end{pmatrix} \quad (6)$$

$$b = \begin{pmatrix} -U_1 \\ -U_2 \\ \vdots \\ -U_M \end{pmatrix} \quad (7)$$

where S represents an N×M order matrix with $s_{ij}$ as elements, x represents an M order matrix with $x_j$ as elements, p represents an N'th order vector with $p_i$ as elements, A is set as an M×M order matrix and b as an M×1 order matrix, and $U_1$ through $U_M$ represent said lower limit value;

wherein in said Expression (2), an undyed average value $V_j$ and undyed standard deviation $\rho_j$ of the of the j'th fluorochrome are obtained from an average value and dispersion of detection values from each of said photodetectors, obtained by irradiating light on microparticles not marked with the j'th fluorochrome, and a random number, generated following a probability density function $F_j(U_j)$ in Expression (9) is used as said lower limit value $U_j$:

$$F_j(U_j) = \frac{1}{\sqrt{2\pi}\,\rho_j} e^{-\frac{(U_j - V_j)^2}{2\rho_j^2}} \quad (9)$$

4. A fluorescence intensity compensation method, comprising:

receiving, with photodetectors having different input wavelength bands, fluorescence emitted from fluorochromes excited by irradiating light on microparticles multiply-labeled by a plurality of fluorochromes with overlapping fluorescence wavelengths;

collecting detected values for the photodetectors; and obtaining a measurement spectrum, by approximating, from a linear sum of single-stain spectrums obtained from microparticles individually labeled with the fluorochromes;

wherein approximation of said measurement spectrum by the linear sum of said single-stain spectrums is performed using a restricted least-square method;

wherein the intensity of fluorescence emitted from each fluorochrome is calculated by obtaining a parameter $x_j$ (j=1 through M) where an evaluation function shown in the following Expression (1) satisfies the following Expression (2) and also is a smallest value $$\chi^2 = \sum_{i=1}^{N} \left( \frac{p_i - \sum_{j=1}^{M} s_{ij} \cdot x_j}{\sigma_i} \right)^2 \quad (1)$$

$$x_j \geq U_j \quad (2)$$

where $S_{ij}$ represents a detected value of the i'th photodetector in the single-stain spectrum of the j'th fluorochrome, $p_i$ represents a detected value of the i'th photodetector in the measurement spectrum, $\sigma_i$ represents an inverse number of a weight as to a detected value of the i'th photodetector, and $U_j$ represents a lower limit value of the fluorescence intensity of each fluorochrome to be calculated;

wherein said parameter $x_j$ (j=1 through M) is obtained by solving the quadratic programming problem in the following Expressions (12) and (13), and executing the following Expression (14)

$$\text{Minimize } \|Sx' - (p - u)\|_2 \quad (12)$$

$$\text{subject to } x' \geq 0 \quad (13)$$

$$x = x' + U \quad (14)$$

where S represents an N×M order matrix with $s_{ij}$ as elements, x represents an M order matrix with $x_j$ as elements, p represents an N'th order vector with $p_i$ as elements, u represents an N'th order vector with an average value $v_i$ of detected values from the i'th photodetector, obtained by irradiating light on microparticles unmarked with the j'th fluorochrome, as elements, and U represents an M'th order vector with an undyed average value $V_j$ of the j'th fluorochrome obtained from the average value $v_i$ as elements.

5. A fluorescence intensity compensation method, comprising:

receiving, with photodetectors having different input wavelength bands, fluorescence emitted from fluorochromes excited by irradiating light on microparticles multiply-labeled by a plurality of fluorochromes with overlapping fluorescence wavelengths;

collecting detected values for the photodetectors; and obtaining a measurement spectrum, by approximating, from a linear sum of single-stain spectrums obtained from microparticles individually labeled with the fluorochromes;

wherein approximation of said measurement spectrum by the linear sum of said single-stain spectrums is performed using a restricted least-square method;

wherein the intensity of fluorescence emitted from each fluorochrome is calculated by obtaining a parameter $x_j$ (j=1 through M) where an evaluation function shown in the following Expression (1) satisfies the following Expression (2) and also is a smallest value $$\chi^2 = \sum_{i=1}^{N} \left( \frac{p_i - \sum_{j=1}^{M} s_{ij} \cdot x_j}{\sigma_i} \right)^2 \quad (1)$$

$$x_j \geq U_j \quad (2)$$

where $S_{ij}$ represents a detected value of the i'th photodetector in the single-stain spectrum of the j'th fluorochrome, $p_i$ represents a detected value of the i'th photodetector in the measurement spectrum, $\sigma_i$ represents an inverse number of a weight as to a detected value of the i'th photodetector, and $U_j$ represents a lower limit value of the fluorescence intensity of each fluorochrome to be calculated;

wherein said parameter $x_j$ (j=1 through M) is obtained by solving the quadratic programming problem in the following Expressions (15) and (16), and executing the following Expression (17)

$$\text{Minimize } \|Sx'-(p-u)\|_2 \quad (15)$$

$$\text{subject to } x' \geq 0 \quad (16)$$

$$x = x' + U \quad (17)$$

where S represents an N×M order matrix with $s_{ij}$ as elements, x represents an M order matrix with $x_j$ as elements, p represents an N'th order vector with $p_i$ as elements, u represents an N'th order vector with random numbers $u_i$ generated following a probability density function $f_i(u_i)$ of a detection value of the i'th photodetector, obtained by irradiating light on microparticles unmarked with the j'th fluorochrome, as elements, and U represents an M'th order vector with random numbers $U_j$ generated following an undyed probability density function $F_j(U_j)$ of the j'th fluorochrome obtained from the probability density function $f_i(u_i)$ as elements.

6. A fluorescence intensity compensation method, comprising:

receiving, with photodetectors having different input wavelength bands, fluorescence emitted from fluorochromes excited by irradiating light on microparticles multiply-labeled by a plurality of fluorochromes with overlapping fluorescence wavelengths;

collecting detected values for the photodetectors; and obtaining a measurement spectrum, by approximating, from a linear sum of single-stain spectrums obtained from microparticles individually labeled with the fluorochromes;

wherein approximation of said measurement spectrum by the linear sum of said single-stain spectrums is performed using a restricted least-square method;

wherein the intensity of fluorescence emitted from each fluorochrome is calculated by obtaining a parameter $x_j$ (j=1 through M) where an evaluation function shown in the following Expression (1) satisfies the following Expression (2) and also is a smallest value $$\chi^2 = \sum_{i=1}^{N} \left( \frac{p_i - \sum_{j=1}^{M} s_{ij} \cdot x_j}{\sigma_i} \right)^2 \quad (1)$$

$$x_j \geq U_j \quad (2)$$

where $S_{ij}$ represents a detected value of the i'th photodetector in the single-stain spectrum of the j'th fluorochrome, $p_i$ represents a detected value of the i'th photodetector in the measurement spectrum, $\sigma_i$ represents an inverse number of a weight as to a detected value of the i'th photodetector, and $U_j$ represents a lower limit value of the fluorescence intensity of each fluorochrome to be calculated;

wherein said parameter $x_j$ (j=1 through M) is obtained by solving the quadratic programming problem in the following Expressions (20) and (21), and executing the following Expression (22)

$$f_i(u_i) = \frac{1}{\sqrt{2\pi}\,\sigma_i} e^{-\frac{(u_i - v_i)^2}{2\sigma_i^2}} \quad (18)$$

$$F_j(U_j) = \frac{1}{\sqrt{2\pi}\,\rho_j} e^{-\frac{(U_j - V_j)^2}{2\rho_j^2}} \quad (19)$$

$$\text{Minimize } \|Sx' - (p-u)\|_2 \quad (20)$$

$$\text{subject to } x' \geq 0 \quad (21)$$

$$x = x' + U \quad (22)$$

where S represents an N×M order matrix with $s_{ij}$ as elements, x represents an M order matrix with $x_j$ as elements, p represents an N'th order vector with $p_i$ as elements, u represents an N'th order vector with a random number $u_j$ generated by obtaining an average value $V_j$ and dispersion $\sigma_i$ of the of the i'th photodetector, obtained by irradiating light on microparticles not marked with the j'th fluorochrome, and generating a random number $u_j$ following a probability density function $f_j(u_j)$ in Expression (18), as the elements, and U represents an M'th order vector having as the elements a random number $U_j$ generated by obtaining the undyed average value $V_j$ and undyed standard deviation $\rho_j$ of the j'th fluorochrome from an average value $v_i$ and dispersion $\sigma_i$ and generating the random number $U_j$ following a probability density function $F_j(U_j)$ in Expression (19).

\* \* \* \* \*